(12) United States Patent
Lennartz et al.

(10) Patent No.: US 7,723,494 B2
(45) Date of Patent: *May 25, 2010

(54) YELLOW ANIONIC DISAZO DYES

(75) Inventors: Michael Lennartz, Lörrach (DE); Adolf Käser, Bottmingen (CH); Sandra Weiss, Lörrach-Brombach (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 57 days.

This patent is subject to a terminal disclaimer.

(21) Appl. No.: 12/006,730

(22) Filed: Jan. 4, 2008

(65) Prior Publication Data

US 2008/0114158 A1    May 15, 2008

Related U.S. Application Data

(62) Division of application No. 10/517,410, filed as application No. PCT/EP03/05561 on May 27, 2003, now Pat. No. 7,341,607.

(30) Foreign Application Priority Data

Jun. 6, 2002    (EP) .................................. 02405456

(51) Int. Cl.
    C09B 35/023    (2006.01)
    C09B 35/03     (2006.01)
    C09B 35/033    (2006.01)
    C09B 35/28     (2006.01)

(52) U.S. Cl. ........................ 534/671; 534/741; 534/745; 534/750; 534/759; 534/764; 8/527; 8/696; 8/916; 8/919; 8/920

(58) Field of Classification Search ........................ None
See application file for complete search history.

(56) References Cited

U.S. PATENT DOCUMENTS

| 2,228,321 A | 1/1941 | Messmer .................... 260/178 |
| 2,544,087 A | 3/1951 | Hindermann ............... 260/160 |
| 3,078,266 A | 2/1963 | Hanhart ...................... 534/708 |
| 4,213,897 A | 7/1980 | Moser et al. ................. 534/606 |
| 5,545,724 A | 8/1996 | Moser ......................... 534/604 |
| 5,545,725 A | 8/1996 | Käser et al. ................. 534/759 |
| 7,341,607 B2 * | 3/2008 | Lennartz et al. ................. 8/696 |

FOREIGN PATENT DOCUMENTS

GB    902228    8/1962

OTHER PUBLICATIONS

Czajkowski, Chemical Abstracts, 127:82800, 1997.*
Czajkowski, Wojciech, "Synthesis and Study of Properties of New Disazo Lakes", Przemysl Chemiczny, 7696), 269-270, 1997.*

* cited by examiner

Primary Examiner—Fiona T Powers
(74) Attorney, Agent, or Firm—Tyler A. Stevenson

(57) ABSTRACT

The present invention relates to novel yellow anionic dyes, a process for their preparation, certain novel intermediates necessary for their preparation and the use of these dyes for dyeing natural or synthetic materials, in particular, paper.

9 Claims, No Drawings

YELLOW ANIONIC DISAZO DYES

This application is a divisional of U.S. application Ser. No. 10/517,410 filed Dec. 3, 2004, now U.S. Pat. No. 7,341,607, which is a 371 of international application No. PCT/EP03/05561, filed May 27, 2003, the contents of which applications are incorporated by reference.

The present invention relates to novel yellow anionic dyes, a process for their preparation, certain novel intermediates necessary for their preparation and the use of these dyes for dyeing natural or synthetic materials, in particular, paper.

The use of diaminobenzanilides as building blocks for the synthesis of bisazo dyes and the advantages thereof has been described in Dyes and Pigments, 17, 297-302 (1991). On this basis, a number of bisazo orange and yellow dyes containing pyrazolones and phenolic derivatives as coupling components have been described, for example, in DE 2,362,995 and in JP 51-11817, whilst further symmetrical bisazo dyes containing 1-phenyl-5-amino pyrazoles have also been reported in U.S. Pat. No. 5,545,725.

However, a requirement exists to provide further anionic dyes especially of neutral or greenish yellow shades, which dyes exhibit excellent degrees of exhaustion with high colour strength, whilst being sufficiently water-soluble to provide stable aqueous formulations without the need for large quantities of solubilizers. Furthermore, dyings obtained should exhibit high degrees of bleed- and light-fastness, be even- or top-sided and be readily bleachable.

Surprisingly, it has now been found that certain bisazo dyes based on diaminobenzanilides exhibit excellent effects with respect to the desired properties.

Accordingly, the invention relates to compounds of the formula

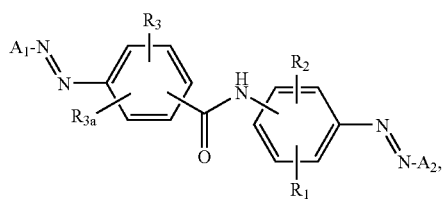

(1)

in which
$R_1$ represents hydrogen, substituted or unsubstituted $C_1$-$C_8$alkyl, substituted or unsubstituted $C_1$-$C_8$alkoxy or $SO_3H$,
$R_2$ represents $SO_3H$ or $CO_2H$,
$R_3$ and $R_{3a}$, each, independently of the other, represent hydrogen, a $C_1$-$C_4$alkyl group, which may be substituted or unsubstituted, halogen, hydroxy, substituted or unsubstituted $C_1$-$C_4$alkoxy, carboxy, $NH_2$ or $NHC_1$-$C_4$alkyl and each of the residues
$A_1$ and $A_2$, independently of the other, is derived from a coupling component selected from the group consisting of an acetoacetylated amine of the formula

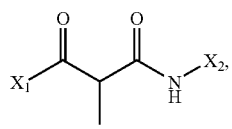

(2)

in which
$X_1$ represents $C_1$-$C_4$alkyl, or phenyl which is unsubstituted or monosubstituted by $C_1$-$C_4$alkyl, $C_1$-$C_4$alkoxy or halogen and
$X_2$ represents phenyl which is unsubstituted, mono-, di- or trisubstituted by one or two $SO_3H$, $SO_2NHC_1$-$C_4$ alkyl groups which alkyl groups may be substituted, $SO_2C_1$-$C_4$alkyl, $C_1$-$C_4$substituted or unsubstituted alkyl, hydroxy, $C_1$-$C_4$alkoxy, halogen, $CF_3$, $NH_2$, $NHCOC_1$-$C_4$alkyl, $NHCOOC_1$-$C_4$alkyl, $NHCONHC_1$-$C_4$alkyl, $CO_2H$, $CONHC_1$-$C_4$alkyl or $NO_2$; a 1- or 2-naphthyl residue which is unsubstituted or substituted by one or two $SO_3H$, $SO_2NHC_1$-$C_4$alkyl, carboxy, $CONHC_1$-$C_4$alkyl, carboxy$C_1$-$C_4$alkyl or carboxyaryl groups or a 5- or 6-membered heterocyclic ring containing 1-3 heteroatoms and which may be benzannelated and be further substituted by $C_1$-$C_4$alkyl, $C_1$-$C_4$alkoxy or halogen and which may be attached to the NH-atom in formula (2) either via the hetero- or benzo-nucleus, in the case of benzannelated heterocycles;

a derivative of barbituric acid of the formula

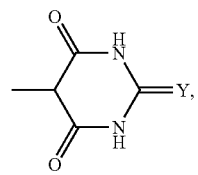

(3)

in which
Y represents O, NCN or $NCONH_2$;
a 2,4,6-triaminopyrimidine;
a pyridone derivative of the formula

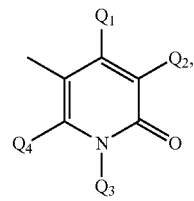

(4)

in which
$Q_1$ represents hydrogen, hydroxy, $C_1$-$C_2$alkyl, hydroxyethyl, 2-($C_1$-$C_2$alkoxy)alkyl, $C_1$-$C_2$alkoxy, COOH, $CONH_2$ or COO $C_1$-$C_2$alkyl, $Q_2$ represents hydrogen, CN, halogen, $SO_3H$ or $C_1$-$C_2$alkyl which is unsubstituted or substituted by hydroxy, phenyl or $SO_3H$, $Q_3$ represents hydrogen, phenyl, $C_1$-$C_2$alkylphenyl, cyclohexyl or $C_1$-$C_4$alkyl which is unsubstituted or substituted by hydroxy, CN, $C_1$-$C_2$alkoxy or $SO_3H$ and $Q_4$ represents hydrogen or hydroxy;

an aminopyrazole or a pyrazolone derivative of formula

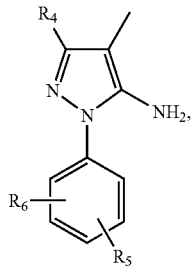
(5)

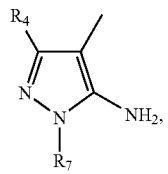
(6)

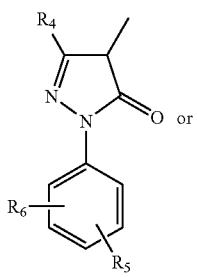
or
(7)

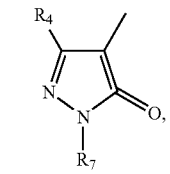
(8)

in which
R₄ represents hydrogen, substituted or unsubstituted $C_1$-$C_4$alkyl, $C_2$-$C_4$alkenyl, NHCO $C_1$-$C_4$alkyl or $CO_2H$, each
$R_5$ and $R_6$, independently of the other, represent hydrogen, halogen, $C_1$-$C_4$alkyl, $SO_3H$ or $CO_2H$ and
$R_7$ represents hydrogen or $C_1$-$C_4$alkyl;
a benzoic acid derivative of formula

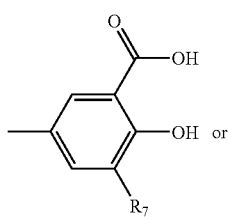
(9)

or

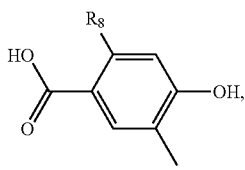
(10)

in which
$R_7$ represents hydrogen or $C_1$-$C_4$alkyl and
$R_8$ represents hydrogen or hydroxy or
$A_1$ and $A_2$, each one independently of the other, represent a phenol residue of the formula

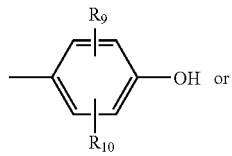
(11)

or

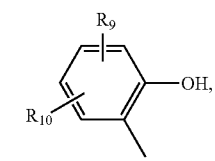
(12)

in which
$R_9$ and $R_{10}$, each one independently of the other, represent hydrogen, $C_1$-$C_4$alkyl, $C_1$-$C_4$alkoxy, hydroxy, halogen, $NH_2$, NHCO $C_1$-$C_4$alkyl, $NO_2$, $SO_3H$, $CO_2C_1$-$C_4$alkyl or CONH$C_1$-$C_4$alkyl groups,
with the proviso that in compounds of formula

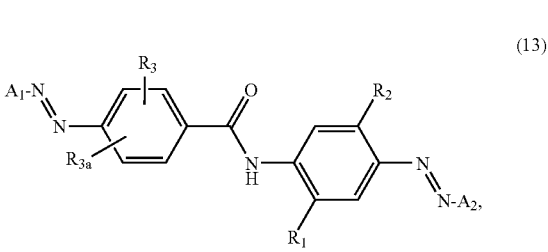
(13)

if
$R_1$, $R_2$, $R_3$ and $R_3$, each, independently of the others, are hydrogen or $SO_3H$, then
$A_1$ and $A_2$ are not both a 1-phenyl or 1-sulphophenyl-3-methyl-5-aminopyrazole residue, or, if
$R_1$, $R_2$, $R_3$ and $R_3$, represent hydrogen and
$A_1$ is a residue of formula (9) in which
$R_7$ represents hydrogen or methyl, then
$A_2$ does not represent a 1-phenyl or 1-sulphophenyl-3-methyl- or 3-carboxy pyrazol-5-one residue or, if
$R_1$, $R_3$ and $R_3$, are hydrogen and $R_2$ is $SO_3H$ and one of
$A_1$ and $A_2$ represents a 1-sulphophenyl-3-methylpyrazol-5-one residue, then the other is not a residue of formula (11) in which both
$R_9$ and $R_{10}$ are hydrogen.

In one preferred aspect of the invention, the compounds of formula (1), contain a total number of two, three or four $SO_3H$ and/or $CO_2H$ groups. These sulphonic and/or carboxylic acid groups may be represented either, as written, in the form of the free acid or in the salt form, $SO_3M$ and/or $CO_2M$. M is preferably one equivalent of a colourless cation, typically lithium, sodium, potassium, ammonium or the protonated form of a $C_4$-$C_{12}$trialkylamine, $C_4$-$C_{12}$diamine, $C_2$-$C_{12}$alkanolamine or of a polyglycol amine, conveniently, triethanolamine trisglycol ether, or mixtures of such cationic species.

M as a protonated $C_4$-$C_{12}$trialkylamine may, for example, be a protonated N-ethyl-dimethylamine, N,N-diethylmethylamine, tri-n-propylamine, tri-n-butylamine, tri-isobutylamine, and, preferably, triethylamine or triisopropylamine.

M as a protonated $C_4$-$C_{12}$diamine may, for example, be ethylenediamine, or 1,3-diaminopropane, in which one or both nitrogen atoms are additionally substituted by one or two $C_1$-$C_4$alkyl radicals, preferably methyl or ethyl radicals. M is preferably an N,N-dialkylethylenediamine or N,N-dialkyl-1,3-diaminopropane. Illustrative examples are: N-ethylethylenediamine, N,N-dimethylethylenediamine, N,N'-dimethylethylenediamine, N,N-diethylethylenediamine, 3-dimethylamino-1-propylamine or 3-diethylamino-1-propylamine. M as a protonated $C_2$-$C_{12}$alkanolamine may be the protonated form of a monoalkanolamine, dialkanolamine, monoalkanolmonoalkylamine, monoalkanoldialkylamine, dialkanolalkylamine or trialkanolamine or a mixture of different protonated alkanolamines. Illustrative examples are: protonated 2-aminoethanol, bis(2-hydroxyethyl)amine, N-(2-hydroxyethyl)dimethylamine, N-(2-hydroxyethyl)diethylamine, N,N-bis(2-hydroxyethyl)ethylamine or tris(2-hydroxyethyl)-amine.

One further preferred class of compounds of formula (1) is that of the formula

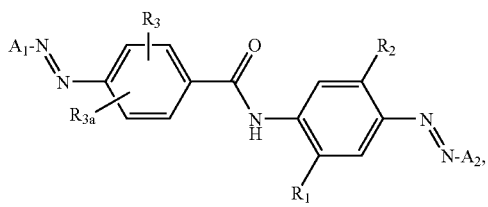

(13)

in which
$R_1$ represents hydrogen, $C_1$-$C_4$alkyl, $C_1$-$C_4$alkoxy or $SO_3H$,
$R_2$ represents $SO_3H$ or $CO_2H$,
$R_3$ represents hydrogen, a $C_1$-$C_4$alkyl group, halogen, hydroxy, $C_1$-$C_4$alkoxy, carboxy, $NH_2$ or $NHC_1$-$C_4$alkyl,
$R_{3a}$ represents hydrogen or $NH_2$ and
$A_1$ and $A_2$ are as defined above.

More preferably, however, in the above compounds of formula (13),
$R_3$ and $R_{3a}$ both represent hydrogen and
$A_1$ and $A_2$, each one independently of the other, is derived from a coupling component selected from the group consisting of
an acetoacetylated amine of the formula

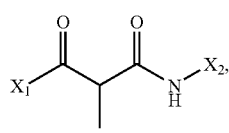

(2)

in which
$X_1$ represents $C_1$-$C_4$alkyl, and
$X_2$ represents phenyl, which is unsubstituted, mono-, di- or trisubstituted by $SO_3H$, $C_1$-$C_4$alkyl, hydroxy, $C_1$-$C_4$alkoxy, halogen or $CO_2H$;
barbituric acid or cyanoiminobarbituric acid;
2,4,6-triaminopyrimidine;
citrazinic acid;
an aminopyrazole or a pyrazolone derivative of formula

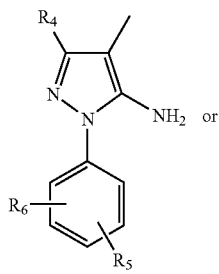

(5)

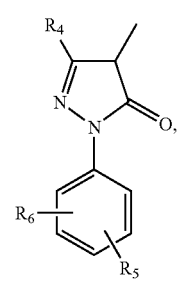

(7)

in which
$R_4$ represents $C_1$-$C_4$alkyl or $CO_2H$,
$R_5$ represents hydrogen, halogen, $C_1$-$C_4$alkyl, $SO_3H$ or $CO_2H$ and
$R_6$ represents hydrogen;
a benzoic acid derivative of formula

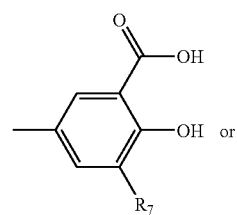

(9)

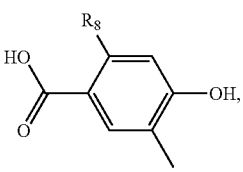

(10)

in which
$R_7$ represents hydrogen or $C_1$-$C_4$alkyl and
$R_8$ represents hydrogen or hydroxy or
$A_1$ and $A_2$, each one independently of the other, represent a phenol residue of the formula

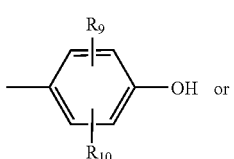
(11)

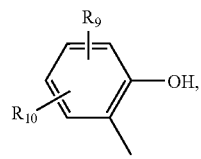
(12)

in which
$R_9$ represents hydrogen, $C_1$-$C_4$alkyl, $C_1$-$C_4$alkoxy, hydroxy, halogen or $SO_3H$ and
$R_{10}$ represents hydrogen.

Most preferred compounds of formula (13) are those in which
$R_1$ represents hydrogen, $C_1$-$C_4$alkoxy, especially methoxy, or $SO_3H$,
$R_2$ represents $SO_3H$ or $CO_2H$,
$R_3$ and $R_{3a}$ both represent hydrogen and the coupling component $A_1$ is derived from an acetoacetylated amine of formula (2), barbituric acid, a compound of formula (5) or (7) in which $R_4$ represents $C_1$-$C_4$alkyl, especially methyl, $R_5$ represents hydrogen or $SO_3H$ and $R_6$ represents hydrogen or from salicyclic acid and the coupling component $A_2$ is derived from an acetoacetylated amine of formula (2), whereby, in formula (2), $X_1$ preferably represents methyl and $X_2$ preferably represents phenyl, which is monosubstituted by $SO_3H$ or trisubstituted by $SO_3H$, methyl and methoxy or $A_2$ is derived from an aminpyrazole of formula (5) in which $R_4$ represents $C_1$-$C_4$alkyl, especially methyl, $R_5$ represents hydrogen or $SO_3H$ and $R_6$ represents hydrogen.

A second preferred class of compounds of formula (1) is that of the formula

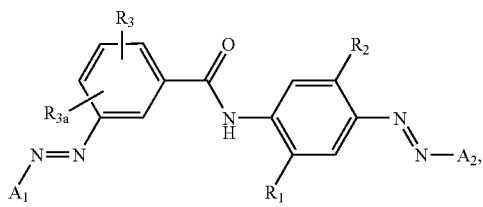
(14)

in which
$R_1$ represents hydrogen, $C_1$-$C_4$alkyl, $C_1$-$C_4$alkoxy or $SO_3H$,
$R_2$ represents $SO_3H$ or $CO_2H$,
$R_3$ represents hydrogen, a $C_1$-$C_4$alkyl group, halogen, hydroxy, $C_1$-$C_4$alkoxy, carboxy, $NH_2$ or $NHC_1$-$C_4$alkyl,
$R^{3a}$ represents hydrogen or $NH_2$ and
$A_1$ and $A_2$ are as defined for formula (1) above.

More preferably, however, in the above compounds of formula (14)
$R_3$ and $R_{3a}$ both represent hydrogen and
$A_1$ and $A_2$, each one independently of the other, is derived from a coupling component selected from the group consisting of
an acetoacetylated amine of the formula

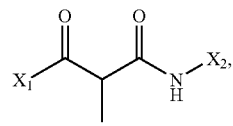
(2)

in which
$X_1$ represents $C_1$-$C_4$alkyl, and
$X_2$ represents phenyl, which is unsubstituted, mono-, di- or trisubstituted by $SO_3H$, $C_1$-$C_4$alkyl, hydroxy, $C_1$-$C_4$alkoxy, halogen or $CO_2H$;
barbituric acid or cyanoiminobarbituric acid;
2,4,6-triaminopyrimidine;
citrazinic acid;
an aminopyrazole or a pyrazolone derivative of formula

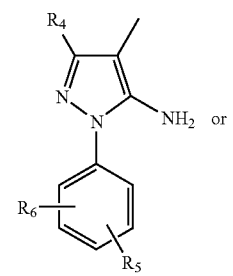
(5)

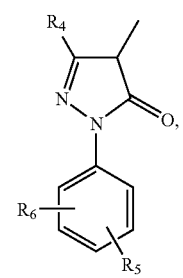
(7)

in which
$R_4$ represents $C_1$-$C_4$alkyl or $CO_2H$,
$R_5$ represents hydrogen, halogen, $C_1$-$C_4$alkyl, $SO_3H$ or $CO_2H$ and
$R_6$ represents hydrogen;
a benzoic acid derivative of formula

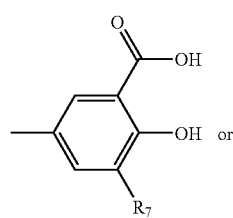
(9)

-continued

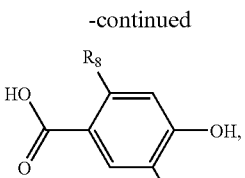
(10)

in which $R_7$ represents hydrogen or $C_1$-$C_4$alkyl and $R_8$ represents hydrogen or hydroxy or $A_1$ and $A_2$, each one independently of the other, represent a phenol residue of the formula

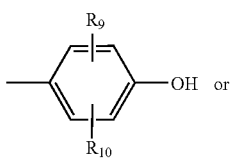
(11)

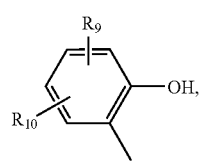
(12)

in which $R_9$ represents hydrogen, $C_1$-$C_4$alkyl, $C_1$-$C_4$alkoxy, hydroxy, halogen or $SO_3H$ and $R_{10}$ represents hydrogen.

Most preferred compounds of formula (14) are those in which $R_1$ represents hydrogen, $C_1$-$C_4$alkoxy, especially methoxy, or $SO_3H$, $R_2$ represents $SO_3H$ or $CO_2H$, $R_3$ and $R_{3a}$ both represent hydrogen and the coupling component $A_1$ is derived from an acetoacetylated amine of formula (2), barbituric acid, cyanoiminobarbituric acid, 2,4,6-triaminopyrimidine, citrazinic acid, a compound of formula (5) or (7) in which $R_4$ represents $C_1$-$C_4$alkyl, especially methyl, $R_5$ represents hydrogen or $SO_3H$ and $R_6$ represents hydrogen or from salicyclic acid, methyl salicyclic acid, phenol or methyl phenol and the coupling component $A_2$ is derived from an acetoacetylated amine of formula (2), whereby, in formula (2), $X_1$ preferably represents methyl and $X_2$ preferably represents phenyl, which is monosubstituted by $SO_3H$ or, especially, trisubstituted by $SO_3H$, methyl and methoxy or $A_2$ is derived from an aminpyrazole of formula (5) in which $R_4$ represents $C_1$-$C_4$alkyl, especially methyl, $R_5$ represents hydrogen or $SO_3H$ and $R_6$ represents hydrogen.

A third preferred class of compounds of formula (1) is that of formula

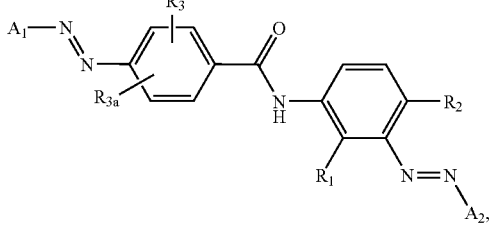
(15)

in which $R_1$ represents hydrogen, $C_1$-$C_4$alkyl, $C_1$-$C_4$alkoxy or $SO_3H$, $R_2$ represents $SO_3H$ or $CO_2H$, $R_3$ represents hydrogen, a $C_1$-$C_4$alkyl group, halogen, hydroxy, $C_1$-$C_4$alkoxy, carboxy, $NH_2$ or $NHC_1$-$C_4$alkyl, $R_{3a}$ represents hydrogen or $NH_2$ and $A_1$ and $A_2$ are as defined for formula (1) above.

More preferably, however, in the above compounds of formula (15)

$R_3$ and $R_{3a}$ both represent hydrogen and $A_1$ and $A_2$, each one independently of the other, is derived from a coupling component selected from the group consisting of an acetoacetylated amine of the formula

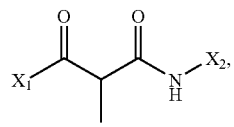
(2)

in which $X_1$ represents $C_1$-$C_4$alkyl, and $X_2$ represents phenyl, which is unsubstituted, mono-, di- or trisubstituted by $SO_3H$, $C_1$-$C_4$alkyl, hydroxy, $C_1$-$C_4$alkoxy, halogen or $CO_2H$;

barbituric acid or cyanoiminobarbituric acid;

2,4,6-triaminopyrimidine;

citrazinic acid;

an aminopyrazole or a pyrazolone derivative of formula

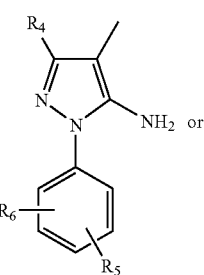
(5)

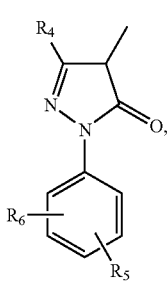

in which
R$_4$ represents C$_1$-C$_4$alkyl or CO$_2$H,
R$_5$ represents hydrogen, halogen, C$_1$-C$_4$alkyl, SO$_3$H or CO$_2$H and
R$_6$ represents hydrogen;
a benzoic acid derivative of formula

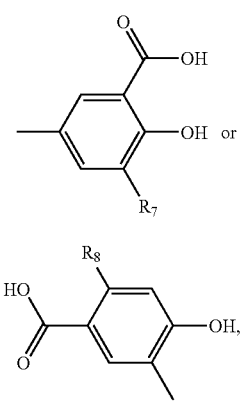

in which
R$_7$ represents hydrogen or C$_1$-C$_4$alkyl and
R$_8$ represents hydrogen or hydroxy or
A$_1$ and A$_2$, each one independently of the other, represent a phenol residue of the formula

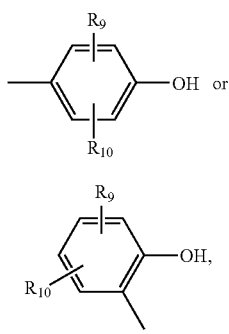

in which
R$_9$ represents hydrogen, C$_1$-C$_4$alkyl, C$_1$-C$_4$alkoxy, hydroxy, halogen or SO$_3$H and
R$_{10}$ represents hydrogen.

Most preferred compounds of formula (15) are those in which
R$_1$ represents hydrogen or C$_1$-C$_4$alkoxy, especially hydrogen,
R$_2$ represents SO$_3$H or CO$_2$H, especially SO$_3$H,
R$_3$ and R$_{3a}$ both represent hydrogen and the coupling component A$_1$ is derived from an acetoacetylated amine of formula (2), barbituric acid, cyanoiminobarbituric acid, triaminopyrimidine, citrazinic acid, a compound of formula (5) or (7) in which R$_4$ represents C$_1$-C$_4$alkyl, especially methyl, R$_5$ represents hydrogen or SO$_3$H and
R$_6$ represents hydrogen or from salicyclic acid, methyl salicyclic acid, phenol or methyl phenol and the coupling component A$_2$ is derived from an acetoacetylated amine of formula (2), whereby, in formula (2), X$_1$ preferably represents methyl and X$_2$ preferably represents phenyl, which is monosubstituted by SO$_3$H or, especially, trisubstituted by SO$_3$H, methyl and methoxy or A$_2$ is derived from an aminpyrazole of formula (5) in which R$_4$ represents C$_1$-C$_4$alkyl, especially methyl, R$_5$ represents hydrogen or SO$_3$H and R$_6$ represents hydrogen.

A fourth preferred class of compounds of formula (1) is that of formula

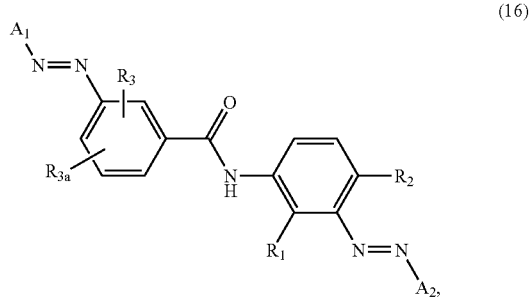

in which
R$_1$ represents hydrogen, C$_1$-C$_4$alkyl, C$_1$-C$_4$alkoxy or SO$_3$H,
R$_2$ represents SO$_3$H or CO$_2$H,
R$_3$ represents hydrogen, a C$_1$-C$_4$alkyl group, halogen, hydroxy, C$_1$-C$_4$alkoxy, carboxy, NH$_2$ or NHC$_1$-C$_4$alkyl,
R$^{3a}$ represents hydrogen or NH$_2$ and
A$_1$ and A$_2$ are as defined for formula (1) above.

More preferably, however, in the above compounds of formula (16),
R$_3$ and R$_{3a}$ both represent hydrogen and
A$_1$ and A$_2$, each one independently of the other, is derived from a coupling component selected from the group consisting of
an acetoacetylated amine of the formula

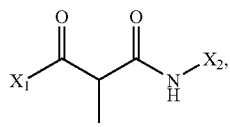

in which
X$_1$ represents C$_1$-C$_4$alkyl, and
X$_2$ represents phenyl, which is unsubstituted, mono-, di- or trisubstituted by SO$_3$H, C$_1$-C$_4$alkyl, hydroxy, C$_1$-C$_4$alkoxy, halogen or CO$_2$H;
barbituric acid or cyanoiminobarbituric acid;

2,4,6-triaminopyrimidine;
citrazinic acid;
an aminopyrazole or a pyrazolone derivative of formula

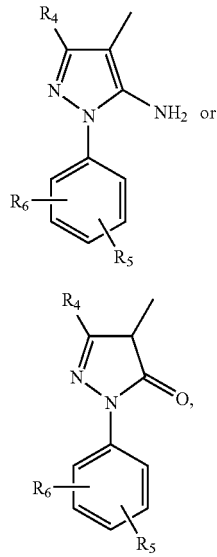

in which
$R_4$ represents $C_1$-$C_4$alkyl or $CO_2H$,
$R_5$ represents hydrogen, halogen, $C_1$-$C_4$alkyl, $SO_3H$ or $CO_2H$ and
$R_6$ represents hydrogen;
a benzoic acid derivative of formula

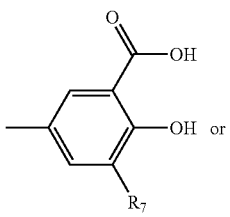

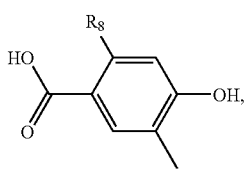

in which
$R_7$ represents hydrogen or $C_1$-$C_4$alkyl and
$R_8$ represents hydrogen or hydroxy or
$A_1$ and $A_2$, each one independently of the other, represent a phenol residue of the formula

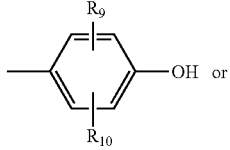

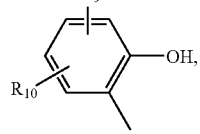

in which
$R_9$ represents hydrogen, $C_1$-$C_4$alkyl, $C_1$-$C_4$alkoxy, hydroxy, halogen or $SO_3H$ and
$R_{10}$ represents hydrogen.

Most preferred compounds of formula (16) are those in which
$R_1$ represents hydrogen or $C_1$-$C_4$alkoxy, especially hydrogen,
$R_2$ represents $SO_3H$ or $CO_2H$, especially $SO_3H$,
$R_3$ and $R_{3a}$ both represent hydrogen and the coupling component $A_1$ is derived from an acetoacetylated amine of formula (2), barbituric acid, cyanoiminobarbituric acid, 2,4,6-triaminopyrimidine, citrazinic acid, a compound of formula (5) or (7) in which $R_4$ represents $C_1$-$C_4$alkyl, especially methyl, $R_5$ represents hydrogen or $SO_3H$ and
$R_6$ represents hydrogen or from salicyclic acid, methyl salicyclic acid, phenol or methyl phenol and the coupling component $A_2$ is derived from an acetoacetylated amine of formula (2), whereby, in formula (2), $X_1$ preferably represents methyl and $X_2$ preferably represents phenyl, which is monosubstituted by $SO_3H$ or, especially, trisubstituted by $SO_3H$, methyl and methoxy or $A_2$ is derived form an aminpyrazole of formula (5) in which $R_4$ represents $C_1$-$C_4$alkyl, especially methyl, $R_5$ represents hydrogen or $SO_3H$ and $R_6$ represents hydrogen.

Within the scope of the definitions of the above formulae and radicals (1) to (16), a $C_1$-$C_8$alkyl radical may be branched or unbranched, for example, methyl, ethyl, n-propyl, isopropyl, n-butyl, sec-butyl, isobutyl, t-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl or 2-ethylhexyl.

Similarly, $C_1$-$C_8$alkoxy may be, for example, methoxy, ethoxy, n-propoxy, isopropoxy, n-butoxy, sec-butoxy, isobutoxy, t-butoxy, 2-ethylbutoxy, n-pentoxy, isopentoxy, 1-methylpentoxy, 1,3-dimethylbutoxy, n-hexyloxy, 1-methylhexyloxy, n-heptyloxy, isoheptyloxy, 1,1,3,3-tetramethylbutoxy, 1-methylheptyloxy, 3-methylheptyloxy, n-octyloxy or 2-ethylhexyloxy When such alkyl or alkoxy radicals are substituted, appropriate substituents may typically include one or two hydroxy, $SO_3H$, carboxy, $C_1$-$C_4$alkoxy, hydroxy-substituted $C_1$-$C_4$alkoxy, phenyl or phenoxy groups. Suitable radicals of this type may include hydroxyethyl, 1-hydroxyisopropyl, ethoxymethyl, 2-hydroxyethoxypentyl, benzyl, 1-phenylethyl, 2-phenylethyl, 1-methyl-2-phenylethyl, 1-isobutyl-3-phenylpropyl or 1-methyl-2-phenoxyethyl.

Halogen in the above formulae and radicals is iodine, bromine, fluorine or, especially, chlorine.

Where, in the derivatives of formulae (4) and (5), $R_4$ represents $C_2$-$C_4$alkenyl, this may, for example, be ethenyl, n-propenyl, isopropenyl, n-butenyl or isobutenyl.

Where, in the acetoacetylated amines of formula (2), $X_2$ represents a 5- or 6-membered heterocyclic ring containing 1-3 heteroatoms and which may be benzannelated, these may be, for example, oxazol-2-yl, thiazol-2-yl, benzoxazol-2-, 5-, or 6-yl, benzothiazol-2-, 5- or 6-yl, benzimidazolone-5-yl, pyrid-2,3- or 4-yl, quinolin-2-, 4-, 5- or 6-yl or 1,3,5-triazin-2-yl radicals.

The dyes of formula (1) of the invention may be prepared by known methods, for example by tetrazotisation of a diaminobenzanilide derivative of the formula

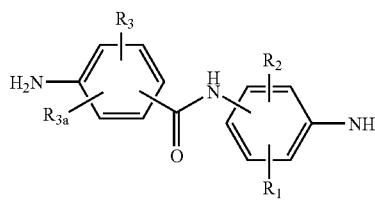
(17)

in which $R_1$, $R_2$, $R_3$ and $R_{3a}$ are as defined for formula (1), and sequential coupling with a coupling component of the formula $A_1H$ or $A_2H$, followed by coupling with a coupling component of the formula $A_2H$ or $A_1H$, $A_2$ and $A_1$ being as defined for formula (1).

Such sequential coupling reactions have been described previously (see, for example, U.S. Pat. No. 5,545,725). However, it is advantageous to perform the initial coupling reaction at a pH value of between 2 and 5, especially between 2.5 and 4, whilst the subsequent coupling reaction is performed at a pH value of between 5 and 9, preferably between 6 and 8.

The coupling components $A_1H$ and $A_2H$ are known compounds or may be prepared by known methods, whilst some of the diaminobenzanilides of formula (14) are novel. Consequently, a further aspect of the invention is a compound of the formula

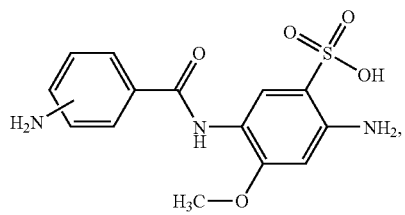
(18)

preferably 4,4'diamino-2'-methoxybenzanilide 5'-sulphonic acid or 3,4'diamino-2'-methoxy-benzanilide 5'-sulphonic acid, a process for the preparation thereof, by reaction of 2-methoxy-4-nitroaniline-5-sulphonic acid with the appropriate nitrobenzoyl halide, preferably m- or p-nitrobenzoyl chloride, followed by reduction of the resulting dinitrobenzanilide by known methods and also the use of the compound (18) for the preparation of the appropriate compound of formula (1).

The dyes of the invention may be used to dye natural or synthetic materials, for example, cellulosic materials, carbonamide group containing materials such as polyamides, leather or glass fibres, but are particularly useful for dyeing paper. They are preferably used as a solid or liquid commercial form.

The pulverulent or granular form of the dye is used particularly in batchwise pulp dyeing where the dye mixture, customarily in the form of a stock solution, is added in the pulper, in the beater or in the mixing chest. Preference is here given to using dye preparations which as well as the dye, may further include extenders, for example urea as solubilizer, dextrin, Glauber salt, sodium chloride and also dispersants, dustproofing agents and sequestrants, such as tetrasodium phosphate.

The present invention accordingly further provides solid dye preparations for dyeing paper comprising a compound of the formula (1) and, optionally, further auxiliaries.

In recent years, the use of concentrated aqueous solutions of dyes has gained importance because of the advantages possessed by such solutions when compared with dyes in powder form. The use of solutions avoids the difficulties associated with dust formation and releases the user from the time-consuming and frequently difficult dissolving of the dye powder in water. The use of concentrated solutions was also prompted by the development of continuous dyeing processes for paper, since it is convenient in these processes to meter the solution directly into the pulp stream or to add it at some other suitable point of the paper-making process.

The present invention accordingly further provides aqueous solutions, preferably concentrated solutions, for dyeing paper, comprising a compound of the formula (1), preferably in a concentration of from 5 to 30% by weight. Due to their excellent solubility in water, the dyes of formula (1) are particularly suitable for the preparation of such solutions.

The concentrated solutions preferably contain a low level of inorganic salts, which may be achieved, if necessary, by known methods, for example reverse osmosis.

The solutions may include further auxiliaries, for example solubilizers such as ε-caprolactam or urea, organic solvents, for example glycols, polyethylene glycols, dimethyl sulphoxide, N-methylpyrrolidone, acetamide, alkanolamines or polyglycolamines, which is a still further aspect of the invention.

In addition, the aqueous dye solutions of the present invention may be applied to paper by use of the so-called spraying technique.

The novel dyes of the invention dye paper in predominantly yellow shades with excellent degrees of exhaustion with high colour strength, whilst being sufficiently water-soluble to provide stable aqueous formulations without the need for large quantities of solubilizers. Furthermore, dyings obtained exhibit high degrees of bleed- and light-fastness, are even- or top-sided and readily bleachable.

Furthermore, as a result of their high colour strength and water solubility, the novel dyes of the invention are suitable for use in the ink-jet printing method.

Consequently, one further aspect of the invention is paper which is dyed with a compound of the formula (1), either in the form of a solid dye preparation, or an aqueous solution, as described above.

The following Examples serve to illustrate the invention without intending to be restrictive in nature. Parts and percentages are by weight unless otherwise stated.

Synthesis of Intermediate Diaminobenzanilides

EXAMPLE 1

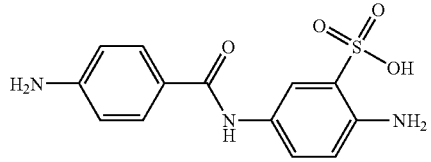
(100a)

73.5 g of p-penylenediamine 2-sulphonic acid are added to 300 g of water and, after addition of approximately 40 g of sodium carbonate, the violet suspension is stirred until solution results. The pH is adjusted to 7.5 by addition of concentrated hydrochloric acid and a solution of 78 g of p-nitrobenzoyl chloride in 100 ml of acetone then added slowly at 25-32° C., the pH being maintained at 6.7-7.0 by addition of 2N aqueous sodium hydroxide. After stirring for a further 1.5 hours, 210 ml of water are added and the pH adjusted to 4.0 by addition of 22 ml of concentrated hydrochloric acid. The readily stirrable suspension is filtered at room temperature and washed with 200 ml of water. The filter cake is then stirred in water at 50° C., filtered hot and dried to yield 75 g of 4'amino-4-nitrobenzanilide 3-sulphonic acid.

A mixture of 1300 g of water, 46.2 g of iron filings and 5.8 g of ammonium chloride is heated to boiling with vigorous stirring and then treated with 55 g of 4'amino-4-nitrobenzanilide 3-sulphonic acid, obtained as described above. The resulting suspension is stirred for a further 1 hour at 95-100° C. and, subsequently, cooled to room temperature. The suspension is filtered hot and the filtrate stirred with 5 g of Hyflo Carcel™ for 30 minutes at room temperature. After filtering, the pH of the hot filtrate is adjusted to 2.0 by addition of 18 g of concentrated hydrochloric acid and the white precipitate filtered and dried. There are obtained 39 g of 4,4'diaminobenzanilide 5'-sulphonic acid of formula (100a).

EXAMPLE 2

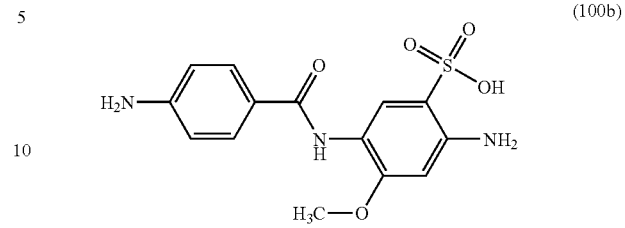
(100b)

74.5 g of 2-methoxy-4-nitroaniline 5-sulphonic acid are added to 300 g of water and, after addition of approximately 30 g of sodium carbonate, the yellowish orange suspension is stirred until solution results. The pH is adjusted to 7.0 by addition of concentrated hydrochloric acid and a solution of 60 g of p-nitrobenzoyl chloride in 75 ml of acetone then added slowly below 28° C., the pH being maintained at 6.7-7.0 by addition of 2N aqueous sodium hydroxide. After stirring for a further 2 hours, 650 g of water are added and the pH adjusted to 4.0 by addition of 2N aqueous hydrochloric acid. The readily stirrable suspension is filtered, the filter cake washed with 200 g of water and sucked dry. There are obtained 391 g of damp filter cake, which is used directly for the next step.

A mixture of 1000 g of water, 60 g of iron filings and 7.6 g of ammonium chloride is heated to boiling with vigorous stirring and then treated with 145 g of the damp filter cake, obtained as described above. The resulting suspension is stirred for a further 2 hours at 90-95° C. and, subsequently, 700 g of water are added. The suspension is filtered hot and the filtrate stirred with 10 g of Hyflo Supercel™ for 30 minutes at 85° C. After filtering, the pH of the hot filtrate is adjusted to 3.8 by addition of 24 g of concentrated hydrochloric acid and the white precipitate filtered and dried. There are obtained 34.3 g of 4,4'diamino-2'-methoxybenzanilide 5'-sulphonic acid of formula (100b).

EXAMPLES 3-10

By following the procedure described in Examples 1 or 2, employing appropriate starting materials, the following benzanilides may be obtained, as summarized in Table 1 below.

TABLE 1

| Example Nr. | Compound Nr | Formula |
|---|---|---|
| 3 | (100c) | |
| 4 | (100d) | |

TABLE 1-continued
| Example Nr. | Compound Nr | Formula |
|---|---|---|
| 5 | (100e) | H₂N–C₆H₄–C(O)–NH–C₆H₃(NH₂)(SO₃H) |
| 6 | (100f) | 3-H₂N–C₆H₄–C(O)–NH–C₆H₃(NH₂)(SO₃H) |
| 7 | (100g) | H₂N–C₆H₄–C(O)–NH–C₆H₂(SO₃H)₂(NH₂) |
| 8 | (100h) | 3-H₂N–C₆H₄–C(O)–NH–C₆H₂(SO₃H)₂(NH₂) |
| 9 | (100i) | H₂N–C₆H₄–C(O)–NH–C₆H₃(CO₂H)(NH₂) |
| 10 | (100j) | 3-H₂N–C₆H₄–C(O)–NH–C₆H₃(CO₂H)(NH₂) |
Synthesis of Dyes
EXAMPLE 11
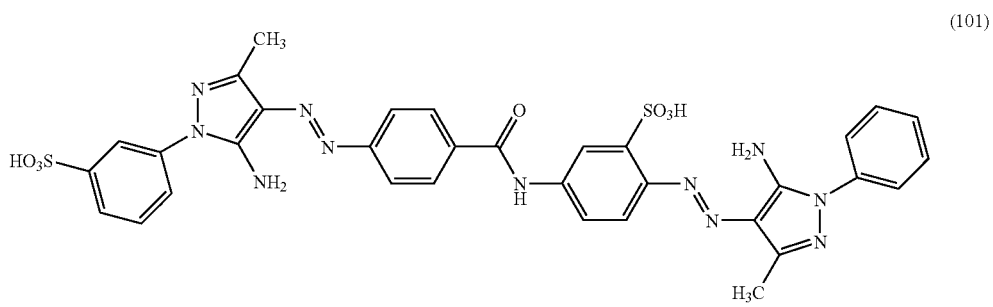
(101)

3.1 g of the compound of formula (100a) are suspended in 50 g of water and 5.7 g of concentrated hydrochloric acid and subsequently treated with 4.75 ml of a 4N aqueous sodium nitrite solution at 0-5° C. over a period of 1 hour. The mixture is stirred for a further 1 hour and excess nitrite then destroyed by addition of 0.3 ml of 2N sulphamic acid. The resultant beige suspension is diluted with 60 g of water and then treated with a total of 2.4 g of 5-amino-3-methyl-1-(3-sulphophenyl) pyrazole, in portions, at 5° C., the pH being maintained at 3.6-4.0 by addition of a total of 13.7 ml of 2N aqueous sodium hydroxide solution. The resulting monoazo suspension is then added slowly, during 70 minutes, to a solution of 1.7 g of 5-amino-3-methyl-1-phenyl pyrazole dissolved in 50 g of water and 50 g of dimethyl formamide, the pH being maintained at 6.5 by addition of a total of 11.9 ml of 2N aqueous sodium hydroxide solution. After stirring for a further 1.5 hours at room temperature, 50 ml of isopropanol and 30 g of sodium chloride are added, the mixture stirred for 1 hour and the resulting yellowish brown suspension filtered. After drying, there are obtained 6.7 g of the compound of formula (101).

EXAMPLE 12

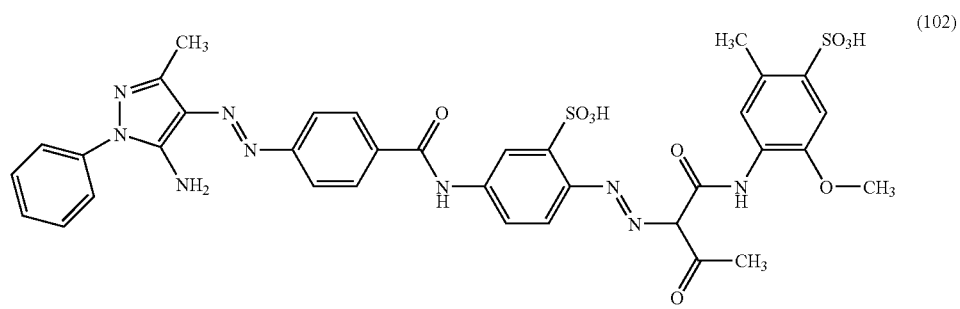

3.1 g of the compound of formula (100a) are suspended in 50 g of water and 5.7 g of concentrated hydrochloric acid and subsequently treated with 4.75 ml of a 4N aqueous sodium nitrite solution at 0-5° C. over a period of 1 hour. The mixture is stirred for a further 1 hour and excess nitrite then destroyed by addition of 0.3 ml of 2N sulphamic acid. The resultant beige suspension is diluted with 60 g of water and then treated with 1.75 g of 5-amino-3-methyl-1-phenyl pyrazole and reaction continued for 2.5 hours at 5° C., the pH being maintained at 3.8-4.0 by addition of a total of 15.9 ml of 2N aqueous sodium hydroxide solution. The resulting monoazo suspension is then added slowly, during 2.5 hours, to a solution of 3.0 g of 3-acetoacetylamino-4-methoxy toluene 6-sulphonic acid dissolved in 50 g of water and 50 g of dimethyl formamide, the pH being maintained at 6.8 by addition of a total of 7 ml of 2N aqueous sodium hydroxide solution. After stirring for a further 1.5 hours at 30-35° C., 75 ml of isopropanol and 45 g of sodium chloride are added and the resulting yellow suspension filtered. After drying, there are obtained 6.8 g of the compound of formula (102).

EXAMPLE 13

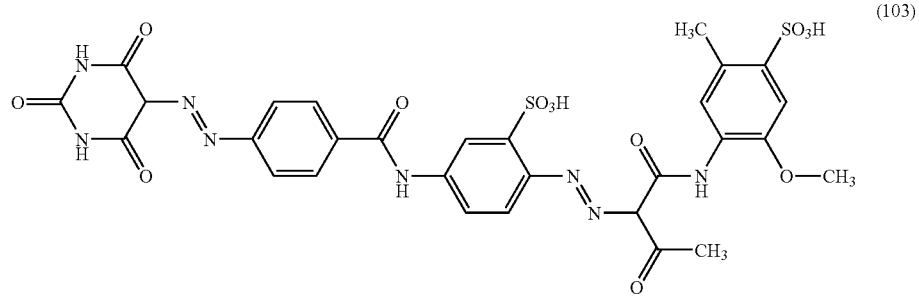

(103)

3.1 g of the compound of formula (100a) are suspended in 50 g of water and 5.7 g of concentrated hydrochloric acid and subsequently treated with 4.75 ml of a 4N aqueous sodium nitrite solution at 0-5° C. over a period of 1 hour. The mixture is stirred for a further 1 hour and excess nitrite then destroyed by addition of 0.3 ml of 2N sulphamic acid. The resultant beige suspension is diluted with 60 g of water and then treated with 1.2 g of barbituric acid. The pH is raised to 2.5 and then maintained at 2.3-2.5 over a period of 3 hours by addition of a total of 5.1 ml of 4N aqueous sodium hydroxide solution. The resulting monoazo suspension is then added slowly, during 1.5 hours, to a solution of 3.5 g of 3-acetoacetylamino-4-methoxy toluene 6-sulphonic acid dissolved in 100 g of water, the pH being maintained at 6.5 by addition of a total of 5.4 ml of 4N aqueous sodium hydroxide solution. After stirring for a further 2.5 hours at room temperature, 75 ml of isopropanol and 15 g of sodium chloride are added and, after stirring briefly at room temperature, the resulting yellowish red suspension is filtered. After drying, there are obtained 7.1 g of the compound of formula (103).

EXAMPLE 14

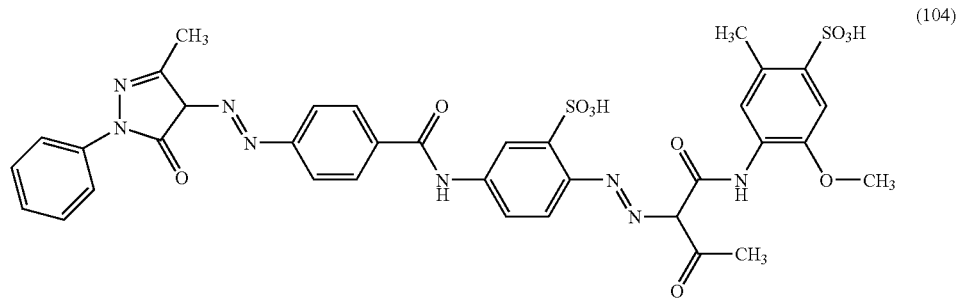

(104)

3.1 g of the compound of formula (100a) are suspended in 50 g of water and 5.7 g of concentrated hydrochloric acid and subsequently treated with 4.75 ml of a 4N aqueous sodium nitrite solution at 0-5° C. over a period of 1 hour. The mixture is stirred for a further 1 hour and excess nitrite then destroyed by addition of 0.3 ml of 2N sulphamic acid. The resultant beige suspension is filtered and the moist presscake suspended in 110 ml of water. 1.75 g of 3-methyl-1-phenyl pyrazo-2-one are added and the pH raised to 3.7. By the addition of a total of 2.5 ml of 4N aqueous sodium hydroxide solution, the pH is maintained at 3.5-4.0, whilst the temperature is raised stepwise from 10° C. to 30° C. After stirring for a total of 3.5 hours the coupling reaction is complete. To the resulting monoazo suspension are then added 50 g of dimethyl formamide followed by 3.5 g of 3-acetoacetylamino-4-methoxy toluene 6-sulphonic acid. The pH is adjusted to 7.0-7.5 and maintained at this value by addition of a further 2.7 ml of 4N aqueous sodium hydroxide solution. After stirring for a further 2 hours at room temperature, 20 g of sodium chloride are added, the mixture stirred for 1 hour at room temperature and the resulting yellow suspension filtered. After drying, there are obtained 5.5 g of the compound of formula (104).

EXAMPLE 15

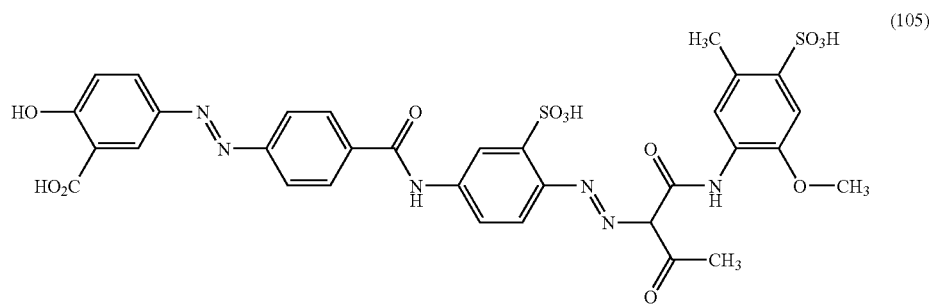

3.1 g of the compound of formula (100a) are suspended in 50 g of water and 5.7 g of concentrated hydrochloric acid and subsequently treated with 4.75 ml of a 4N aqueous sodium nitrite solution at 0-5° C. over a period of 1 hour. The mixture is stirred for a further 1 hour and excess nitrite then destroyed by addition of 0.3 ml of 2N sulphamic acid. The resultant beige suspension is filtered and the moist presscake suspended in 110 ml of water. 1.4 g of salicylic acid are added and the pH raised to 3.0-3.3. By the addition of a total of 4.9 ml of 2N aqueous sodium hydroxide solution, the pH is maintained at 3.0-3.5. After stirring for a total of 2.5 hours at room temperature the coupling reaction is complete. To the resulting monoazo suspension are then added 3.5 g of 3-acetoacetylamino-4-methoxy toluene 6-sulphonic acid. The pH is adjusted to 6.5 and maintained at this value by addition of a further 4.9 ml of 2N aqueous sodium hydroxide solution. After stirring for a total of 3.5 hours at room temperature, 10 g of sodium chloride and 15 ml of isopropanol are added, the pH increased to 8.5 and the resulting yellowish brown suspension filtered. After drying, there are obtained 5.2 g of the compound of formula (105).

EXAMPLES 16-116

By proceeding in an analogous manner to that described in Examples 11-15, but utilizing the appropriate coupling components, compounds of formula (19) are obtained, as summarized in the following Table 2.

TABLE 2

(19)

A'₁—N=N—[benzene]—C(=O)—NH—[benzene with SO₃H]—N=N—A'₂

| Example Nr. | Compound Nr. | A'₁ | A'₂ |
|---|---|---|---|
| 16 | (106) | H₃C-C(=O)-CH(CH₃)-C(=O)-NH-[phenyl: 2-CH₃, 4-SO₃H, 5-OCH₃] | H₃C-C(=O)-CH(CH₃)-C(=O)-NH-[phenyl: 2-CH₃, 4-SO₃H, 5-OCH₃] |
| 17 | (107) | H₃C-C(=O)-CH(CH₃)-C(=O)-NH-[phenyl-4-SO₃H] | H₃C-C(=O)-CH(CH₃)-C(=O)-NH-[phenyl: 2-CH₃, 4-SO₃H, 5-OCH₃] |
| 18 | (108) | H₃C-C(=O)-CH(CH₃)-C(=O)-NH-[phenyl-3-SO₃H] | H₃C-C(=O)-CH(CH₃)-C(=O)-NH-[phenyl: 2-CH₃, 4-SO₃H, 5-OCH₃] |
| 19 | (109) | H₃C-C(=O)-CH(CH₃)-C(=O)-NH-[phenyl: 3-SO₃H, 4-OCH₃] | H₃C-C(=O)-CH(CH₃)-C(=O)-NH-[phenyl: 2-CH₃, 4-SO₃H, 5-OCH₃] |
| 20 | (110) | 5-methyl-2-(cyanoimino)-4,6-dioxohexahydropyrimidine | H₃C-C(=O)-CH(CH₃)-C(=O)-NH-[phenyl: 2-CH₃, 4-SO₃H, 5-OCH₃] |
| 21 | (111) | 2,4,6-triamino-5-methylpyrimidine | H₃C-C(=O)-CH(CH₃)-C(=O)-NH-[phenyl: 2-CH₃, 4-SO₃H, 5-OCH₃] |
| 22 | (112) | 2,6-dihydroxy-3-methyl-4-carboxypyridine | H₃C-C(=O)-CH(CH₃)-C(=O)-NH-[phenyl: 2-CH₃, 4-SO₃H, 5-OCH₃] |

TABLE 2-continued (19)

| Example Nr. | Compound Nr. | A'$_1$ | A'$_2$ |
|---|---|---|---|
| 23 | (113) | 3-(HO$_3$S)-phenyl-, 3-methyl-4-methyl-5-amino-pyrazol-1-yl | 2-methyl-3-oxo-butanoyl-amino-(2-methoxy-5-methyl-4-SO$_3$H)-phenyl |
| 24 | (114) | 4-(HO$_3$S)-phenyl-, 3-methyl-4-methyl-5-OH-pyrazol-1-yl | 2-methyl-3-oxo-butanoyl-amino-(2-methoxy-5-methyl-4-SO$_3$H)-phenyl |
| 25 | (115) | 4-Cl-phenyl-, 3-methyl-4-methyl-5-OH-pyrazol-1-yl | 2-methyl-3-oxo-butanoyl-amino-(2-methoxy-5-methyl-4-SO$_3$H)-phenyl |
| 26 | (116) | 3-Cl-phenyl-, 3-methyl-4-methyl-5-OH-pyrazol-1-yl | 2-methyl-3-oxo-butanoyl-amino-(2-methoxy-5-methyl-4-SO$_3$H)-phenyl |
| 27 | (117) | 4-(HO$_3$S)-phenyl-, 3-methyl-4-methyl-5-OH-pyrazol-1-yl | 2-methyl-3-oxo-butanoyl-amino-(2-methoxy-5-methyl-4-SO$_3$H)-phenyl |
| 28 | (118) | 2,5-dichloro-4-(HO$_3$S)-phenyl-, 3-methyl-4-methyl-5-OH-pyrazol-1-yl | 2-methyl-3-oxo-butanoyl-amino-(2-methoxy-5-methyl-4-SO$_3$H)-phenyl |
| 29 | (119) | 2-chloro-5-(HO$_3$S)-phenyl-, 3-methyl-4-methyl-5-OH-pyrazol-1-yl | 2-methyl-3-oxo-butanoyl-amino-(2-methoxy-5-methyl-4-SO$_3$H)-phenyl |

TABLE 2-continued (19)

| Example Nr. | Compound Nr. | A'$_1$ | A'$_2$ |
|---|---|---|---|
| 30 | (120) | 4-sulfophenyl-pyrazole with 4-methyl, 5-hydroxy, 3-CO$_2$H | acetoacetyl-methyl derivative on 2-methyl-4-sulfo-5-methoxyanilide |
| 31 | (121) | 1-phenyl-pyrazole with 4-methyl, 5-hydroxy, 3-CO$_2$H | acetoacetyl-methyl derivative on 2-methyl-4-sulfo-5-methoxyanilide |
| 32 | (122) | 3-methyl-5-methyl-2-hydroxy-benzoic acid | acetoacetyl-methyl derivative on 2-methyl-4-sulfo-5-methoxyanilide |
| 33 | (123) | 4-hydroxy-3-methylbenzoic acid | acetoacetyl-methyl derivative on 2-methyl-4-sulfo-5-methoxyanilide |
| 34 | (124) | 2,4-dimethylphenol | acetoacetyl-methyl derivative on 2-methyl-4-sulfo-5-methoxyanilide |
| 35 | (125) | 4-tert-butyl-2-methylphenol | acetoacetyl-methyl derivative on 2-methyl-4-sulfo-5-methoxyanilide |
| 36 | (126) | 4-hydroxy-3-methylbenzenesulfonic acid | acetoacetyl-methyl derivative on 2-methyl-4-sulfo-5-methoxyanilide |

TABLE 2-continued (19)

| Example Nr. | Compound Nr. | A'₁ | A'₂ |
|---|---|---|---|
| 37 | (127) | | |
| 38 | (128) | | |
| 39 | (129) | | |
| 40 | (130) | | |
| 41 | (131) | | |
| 42 | (132) | | |
| 43 | (133) | | |

TABLE 2-continued (19)

| Example Nr. | Compound Nr. | A'₁ | A'₂ |
|---|---|---|---|
| 44 | (134) | 3-methyl-4-methyl-5-amino-1-phenylpyrazole | 2-methyl-3-oxo-N-(3-sulfophenyl)butanamide |
| 45 | (135) | 3-methyl-4-methyl-5-hydroxy-1-phenylpyrazole | 2-methyl-3-oxo-N-(3-sulfophenyl)butanamide |
| 46 | (136) | 1-(4-carboxyphenyl)-3-methyl-4-methyl-5-hydroxypyrazole | 2-methyl-3-oxo-N-(3-sulfophenyl)butanamide |
| 47 | (137) | 1-(4-chlorophenyl)-3-methyl-4-methyl-5-hydroxypyrazole | 2-methyl-3-oxo-N-(3-sulfophenyl)butanamide |
| 48 | (138) | 1-(3-chlorophenyl)-3-methyl-4-methyl-5-hydroxypyrazole | 2-methyl-3-oxo-N-(3-sulfophenyl)butanamide |
| 49 | (139) | 1-(4-sulfophenyl)-3-methyl-4-methyl-5-hydroxypyrazole | 2-methyl-3-oxo-N-(3-sulfophenyl)butanamide |
| 50 | (140) | 1-(2,5-dichloro-4-sulfophenyl)-3-methyl-4-methyl-5-hydroxypyrazole | 2-methyl-3-oxo-N-(3-sulfophenyl)butanamide |
| 51 | (141) | 1-(2-chloro-5-sulfophenyl)-3-methyl-4-methyl-5-hydroxypyrazole | 2-methyl-3-oxo-N-(3-sulfophenyl)butanamide |

TABLE 2-continued (19)

| Example Nr. | Compound Nr. | A'₁ | A'₂ |
|---|---|---|---|
| 52 | (142) | 1-(4-sulfophenyl)-3-carboxy-4-methyl-5-hydroxypyrazole | 2-methyl-3-oxo-N-(3-sulfophenyl)butanamide |
| 53 | (143) | 1-phenyl-3-carboxy-4-methyl-5-hydroxypyrazole | 2-methyl-3-oxo-N-(3-sulfophenyl)butanamide |
| 54 | (144) | 2-hydroxy-5-methylbenzoic acid | 2-methyl-3-oxo-N-(3-sulfophenyl)butanamide |
| 55 | (145) | 2-hydroxy-3,5-dimethylbenzoic acid | 2-methyl-3-oxo-N-(3-sulfophenyl)butanamide |
| 56 | (146) | 4-hydroxy-3-methylbenzoic acid | 2-methyl-3-oxo-N-(3-sulfophenyl)butanamide |
| 57 | (147) | 2,4-dimethylphenol (4-hydroxy-1,3-dimethylbenzene) | 2-methyl-3-oxo-N-(3-sulfophenyl)butanamide |
| 58 | (148) | 4-tert-butyl-2-methylphenol | 2-methyl-3-oxo-N-(3-sulfophenyl)butanamide |
| 59 | (149) | 4-sulfo-2-methylphenol | 2-methyl-3-oxo-N-(3-sulfophenyl)butanamide |
| 60 | (150) | 2,4-dimethylphenol | 2-methyl-3-oxo-N-(3-sulfophenyl)butanamide |

TABLE 2-continued
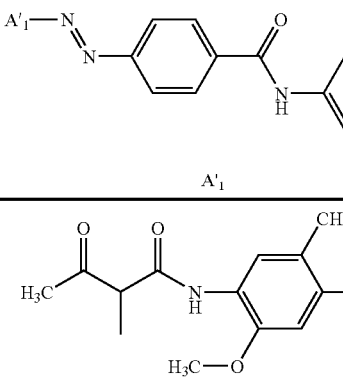
(19)
| Example Nr. | Compound Nr. | A'₁ | A'₂ |
|---|---|---|---|
| 61 | (151) | 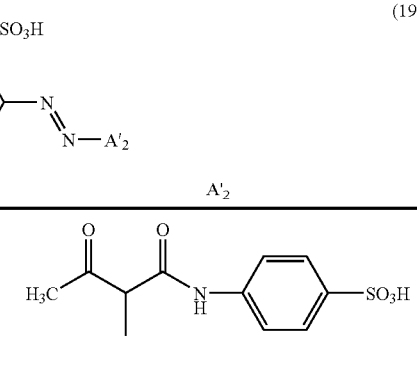 | 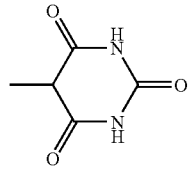 |
| 62 | (152) | 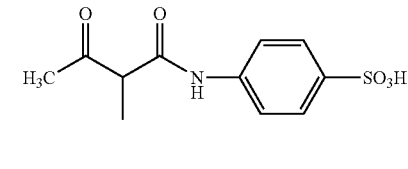 | 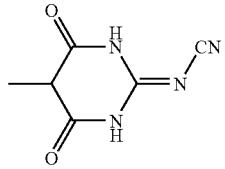 |
| 63 | (153) | 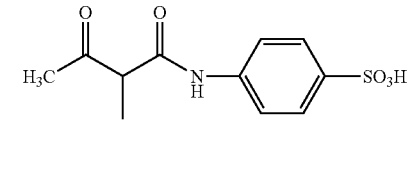 | 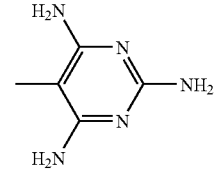 |
| 64 | (154) | 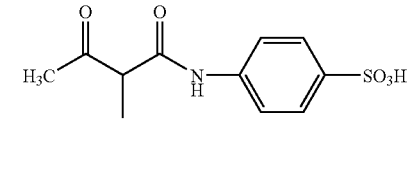 | 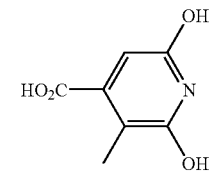 |
| 65 | (155) | 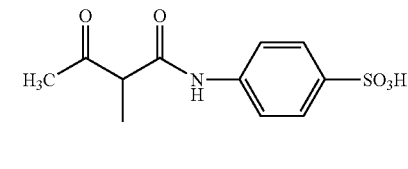 | 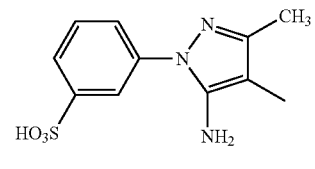 |
| 66 | (156) | 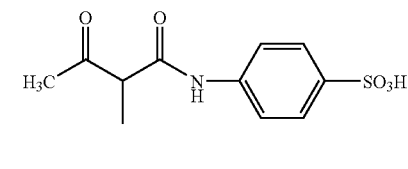 | 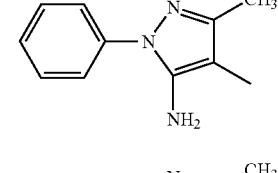 |
| 67 | (157) | 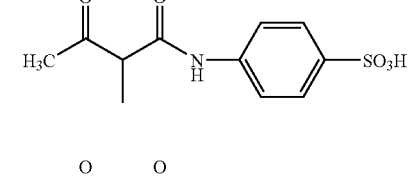 | 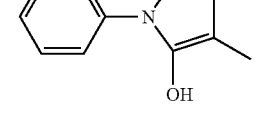 |
| 68 | (158) | 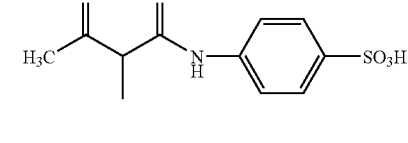 | |

TABLE 2-continued
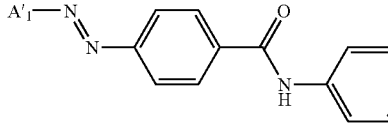
(19)
| Example Nr. | Compound Nr. | A'₁ | A'₂ |
|---|---|---|---|
| 69 | (159) |  | 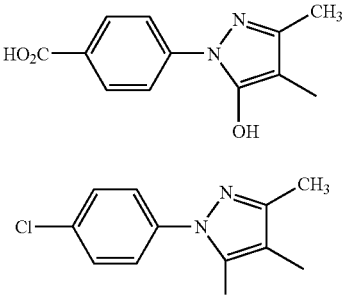 |
| 70 | (160) | 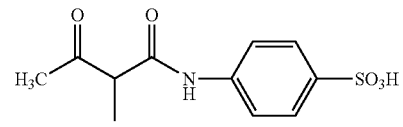 | 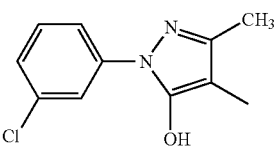 |
| 71 | (161) | 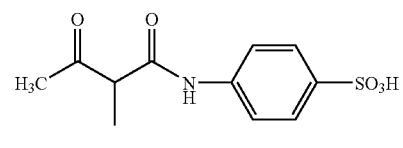 | 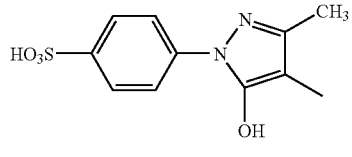 |
| 72 | (162) | 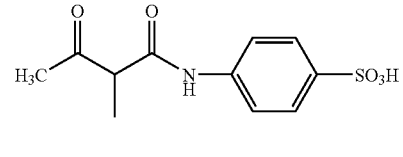 | 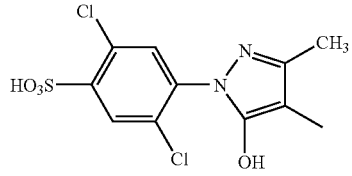 |
| 73 | (163) | 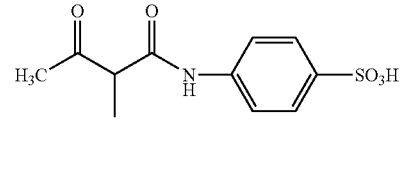 | 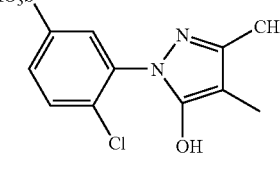 |
| 74 | (164) | 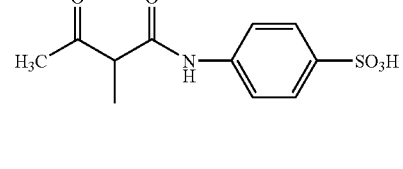 | 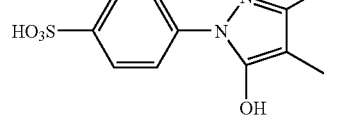 |
| 75 | (165) | 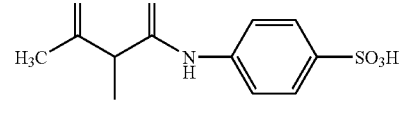 | 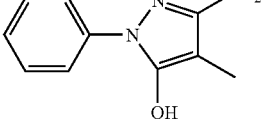 |
| 76 | (166) | 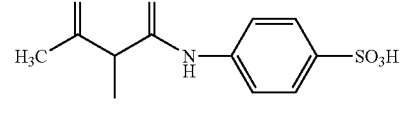 | |

TABLE 2-continued (19)

| Example Nr. | Compound Nr. | A'₁ | A'₂ |
|---|---|---|---|
| 77 | (167) | 5-methyl-2-hydroxybenzoic acid (CO₂H, OH) | H₃C-C(O)-CH(CH₃)-C(O)-NH-C₆H₄-SO₃H |
| 78 | (168) | 3,5-dimethyl-2-hydroxybenzoic acid (CO₂H, OH, CH₃) | H₃C-C(O)-CH(CH₃)-C(O)-NH-C₆H₄-SO₃H |
| 79 | (169) | HO₂C-C₆H₃(CH₃)-OH | H₃C-C(O)-CH(CH₃)-C(O)-NH-C₆H₄-SO₃H |
| 80 | (170) | H₃C-C₆H₃(CH₃)-OH | H₃C-C(O)-CH(CH₃)-C(O)-NH-C₆H₄-SO₃H |
| 81 | (171) | (H₃C)₃C-C₆H₃(CH₃)-OH | H₃C-C(O)-CH(CH₃)-C(O)-NH-C₆H₄-SO₃H |
| 82 | (172) | HO₃S-C₆H₃(CH₃)-OH | H₃C-C(O)-CH(CH₃)-C(O)-NH-C₆H₄-SO₃H |
| 83 | (173) | 2,4-dimethyl-phenol with additional CH₃ | H₃C-C(O)-CH(CH₃)-C(O)-NH-C₆H₄-SO₃H |
| 84 | (174) | H₃C-C(O)-CH(CH₃)-C(O)-NH-C₆H₂(CH₃)(SO₃H)(OCH₃) | 1-(3-sulfophenyl)-3,4-dimethyl-5-amino-pyrazole |
| 85 | (175) | H₃C-C(O)-CH(CH₃)-C(O)-NH-C₆H₄-SO₃H | 1-(3-sulfophenyl)-3,4-dimethyl-5-amino-pyrazole |

TABLE 2-continued
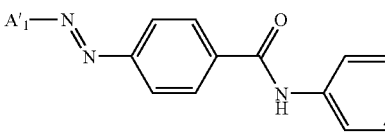
(19)
| Example Nr. | Compound Nr. | A'₁ | A'₂ |
|---|---|---|---|
| 86 | (176) | 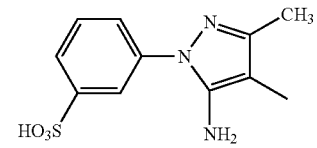 | 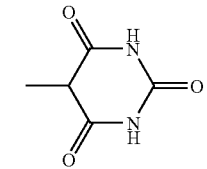 |
| 87 | (177) | 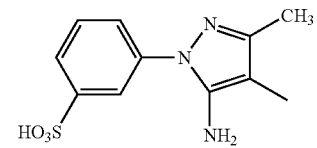 | 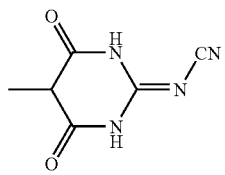 |
| 88 | (178) | 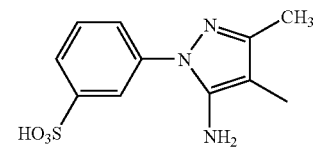 | 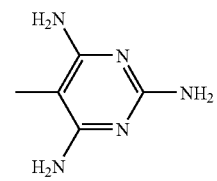 |
| 89 | (179) | 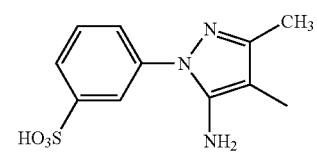 | 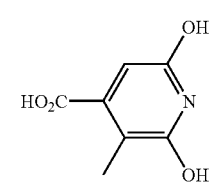 |
| 90 | (180) | 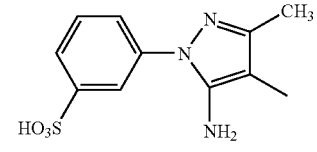 | 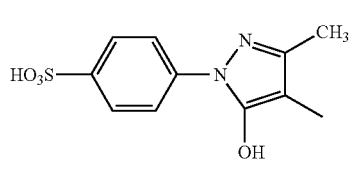 |
| 91 | (181) | 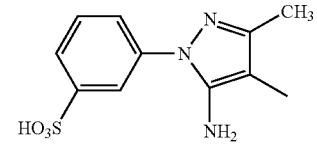 | 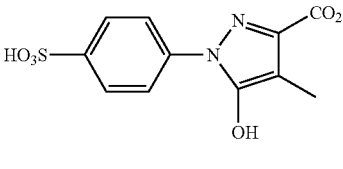 |
| 92 | (182) | 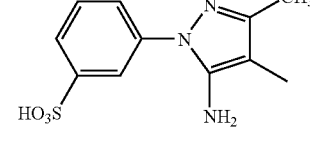 | 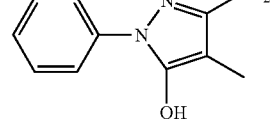 |
| 93 | (183) | 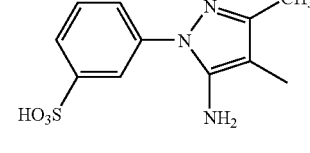 | |

TABLE 2-continued
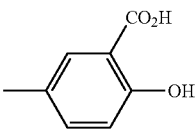
(19)
| Example Nr. | Compound Nr. | A'₁ | A'₂ |
|---|---|---|---|
| 94 | (184) | 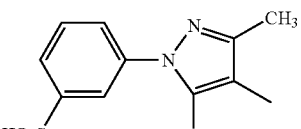 | 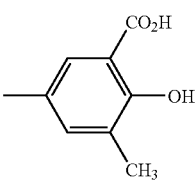 |
| 95 | (185) | 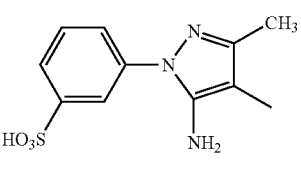 | 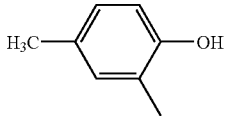 |
| 96 | (186) | 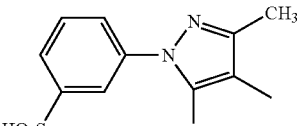 | 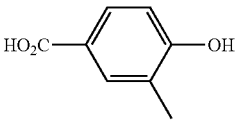 |
| 97 | (187) | 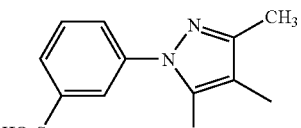 | 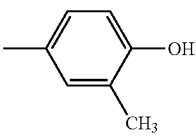 |
| 98 | (188) | 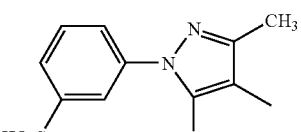 | 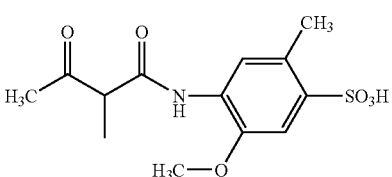 |
| 99 | (189) | 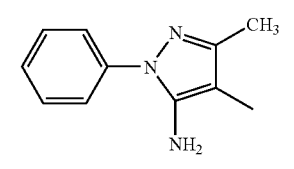 | 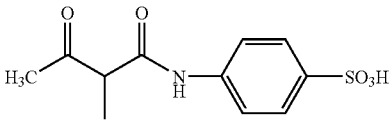 |
| 100 | (190) | 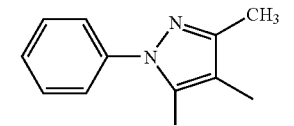 | 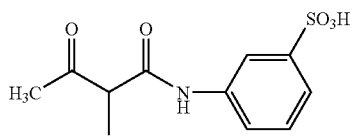 |
| 101 | (191) | 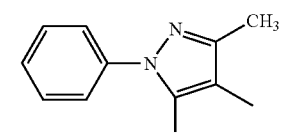 | |

TABLE 2-continued (19)

| Example Nr. | Compound Nr. | A'₁ | A'₂ |
|---|---|---|---|
| 102 | (192) | 4-(HO₂C)phenyl-pyrazole (3-CH₃, 4-CH₃, 5-OH) | 1-phenyl-pyrazole (3-CH₃, 4-CH₃, 5-NH₂) |
| 103 | (193) | 4-(HO₃S)phenyl-pyrazole (3-CH₃, 4-CH₃, 5-OH) | 1-phenyl-pyrazole (3-CH₃, 4-CH₃, 5-NH₂) |
| 104 | (194) | 1-phenyl-pyrazole (3-CO₂H, 4-CH₃, 5-OH) | 1-phenyl-pyrazole (3-CH₃, 4-CH₃, 5-NH₂) |
| 105 | (195) | 2-hydroxy-5-methylbenzoic acid (CO₂H) | 1-phenyl-pyrazole (3-CH₃, 4-CH₃, 5-NH₂) |
| 106 | (196) | 2-hydroxy-3,5-dimethylbenzoic acid | 1-phenyl-pyrazole (3-CH₃, 4-CH₃, 5-NH₂) |
| 107 | (197) | 4-hydroxy-3-methylbenzoic acid | 1-phenyl-pyrazole (3-CH₃, 4-CH₃, 5-NH₂) |
| 108 | (198) | 4-hydroxy-3-methylbenzenesulfonic acid | 1-phenyl-pyrazole (3-CH₃, 4-CH₃, 5-NH₂) |
| 109 | (199) | acetoacetamide derivative (2-CH₃, 5-SO₃H, OCH₃) | 5-methylbarbituric acid |

TABLE 2-continued
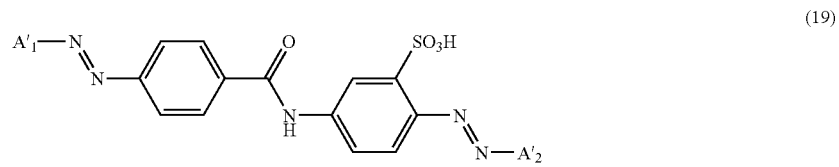
| Example Nr. | Compound Nr. | A'₁ | A'₂ |
|---|---|---|---|
| 110 | (200) | | |
| 111 | (201) | | |
| 112 | (202) | | |
| 113 | (203) | | |
| 114 | (204) | | |
| 115 | (205) | | |
| 116 | (206) | | |

EXAMPLE 117

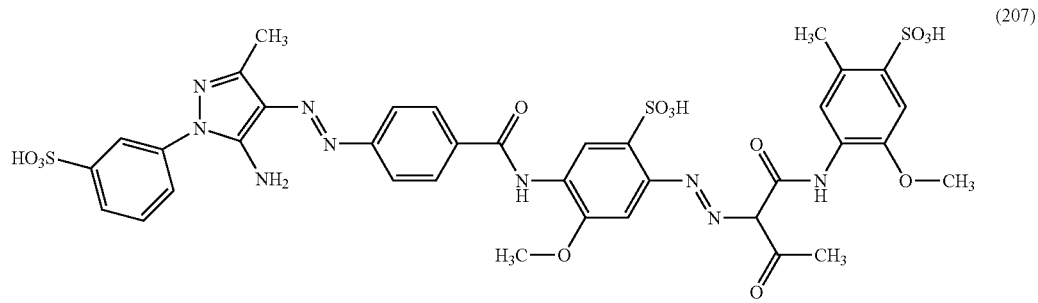
(207)

4.5 g of 4,4'diamino-2'-methoxybenzanilide 5'-sulphonic acid of formula (100b), prepared as described in Example 2, are suspended in 50 g of water and 7.6 g of concentrated hydrochloric acid and subsequently treated with 5.7 ml of 4N aqueous sodium nitrite solution over 1 hour at 0-5° C. The mixture is stirred for a further 1 hour and excess nitrite destroyed by addition of 0.8 ml of 2N aqueous sulphamic acid solution. The resulting yellow suspension is diluted with 60 g of water and treated with 2.9 g of 5-amino-3-methyl-1-(3-sulphophenyl)pyrazole at 5° C., the pH being initially raised to 3.5 and maintained at 3.0-3-5 by the addition of a total of 27.4 ml of 2N aqueous sodium hydroxide solution. After stirring for 2.5 hours the initial coupling reaction is completed. The resulting monoazo suspension is slowly added to a solution of 4.0 g of 3-acetacetylamino-4-methoxytoluene 6-sulphonic acid in 50 g of dimethylformamide over 2.5 hours at 30° C., the pH being maintained at 6.8-7.0 by addition of a total of 7.3 ml of 4N aqueous sodium hydroxide solution. After stirring for 1.5 hours at 30° C., 35 g of sodium chloride and 50 g of isopropanol are added, the mixture stirred over night and the precipitated solids filtered. After drying, there are obtained 10.2 g of the compound of formula (207).

EXAMPLE 118

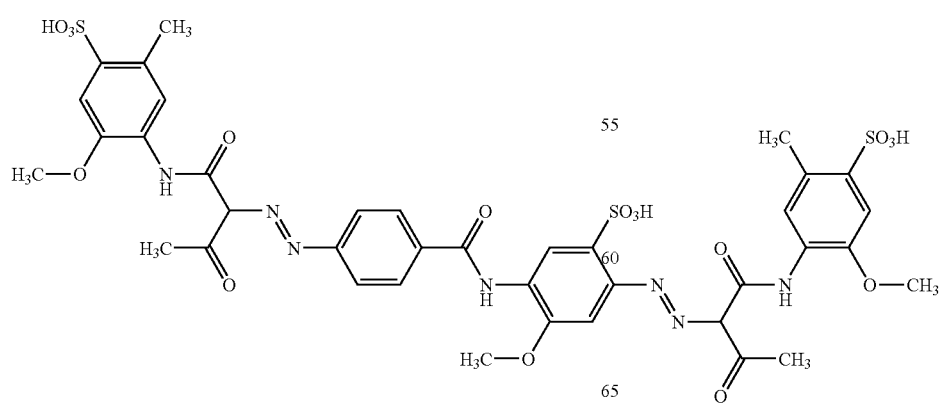
(208)

4.5 g of 4,4'diamino-2'-methoxybenzanilide 5'-sulphonic acid of formula (100b), prepared as described in Example 2, are suspended in 50 g of water and 7.6 g of concentrated hydrochloric acid and subsequently treated with 5.7 ml of 4N aqueous sodium nitrite solution over 1 hour at 0-5° C. The mixture is stirred for a further 1 hour and excess nitrite destroyed by addition of 0.8 ml of 2N aqueous sulphamic acid solution. The resulting yellow suspension is added to a solution of 7.7 g of 3-acetacetylamino-4-methoxytoluene 6-sulphonic acid in 100 g of water over 30 minutes at 5° C., the pH being of which is initially adjusted to 3.8 and is maintained at 3.8-4.0 by the addition of a total of 22.6 ml of 2N aqueous sodium hydroxide solution. Subsequently, the pH is raised to 6.8-7.4 by addition of a further 10.1 ml of 2N aqueous sodium hydroxide solution and the temperature increased to 25-40° C. After stirring for a total of 3 hours, 45 g of potassium chloride and 50 g of isopropanol are added and the precipitated solids filtered. After drying, there are obtained 12.9 g of the compound of formula (208).

EXAMPLE 119

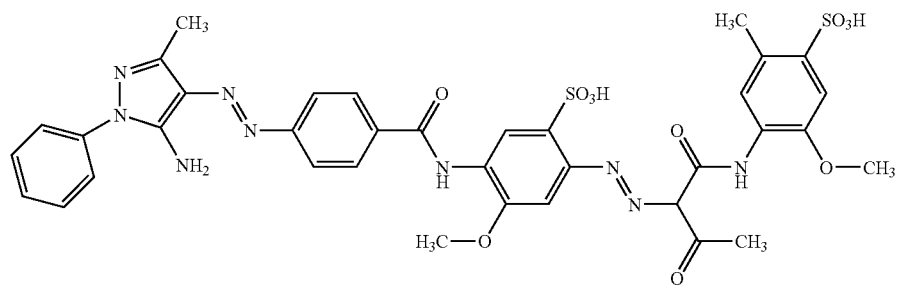

(209)

2.1 g of 4,4'diamino-2'-methoxybenzanilide 5'-sulphonic acid of formula (100b), prepared as described in Example 2, are suspended in 50 g of water and 7.6 g of concentrated hydrochloric acid and subsequently treated with 5.7 ml of 4N aqueous sodium nitrite solution over 1 hour at 0-5° C. The mixture is stirred for a further 1 hour and excess nitrite destroyed by addition of 2N aqueous sulphamic acid solution. The resulting yellow solution is treated with 0.9 g of 5-amino-3-methyl-1-phenyl pyrazole at 5° C., the pH being initially raised to 3.0 and maintained at 2.5-3.0 by the addition of a total of 3.1 ml of 4N aqueous sodium hydroxide solution. After stirring for 2.5 hours and slowly warming to 20° C., the initial coupling reaction is completed. To the resulting monoazo suspension are added 1.7 g of 3-acetacetylamino-4-methoxytoluene 6-sulphonic acid, the pH raised to 6.5 and maintained at 6.0-7.5 by addition of a total of 2.2 ml of 4N aqueous sodium hydroxide solution. After stirring for 3 hours at 20-40° C. reaction is complete and the precipitated solids are filtered. After drying, there are obtained 5.4 g of the compound of formula (209).

EXAMPLES 120-191

By proceeding in an analogous manner to that described in Examples 117-119, but utilizing the appropriate coupling components, compounds of formula (20) are obtained, as summarized in the following Table 3.

TABLE 3

(20)

| Example Nr. | Compound Nr. | A'₁ | A'₂ |
|---|---|---|---|
| 120 | (210) | [structure: H₃C-C(O)-CH(CH₃)-C(O)-NH-C₆H₄-SO₃H (para)] | [structure: H₃C-C(O)-CH(CH₃)-C(O)-NH-aryl with CH₃, SO₃H, OCH₃] |
| 121 | (211) | [structure: H₃C-C(O)-CH(CH₃)-C(O)-NH-C₆H₄-SO₃H (meta)] | [structure: same as above] |
| 122 | (212) | [structure: 5-methylbarbituric acid] | [structure: same acetoacetanilide derivative] |
| 123 | (213) | [structure: 5-methyl-2-(cyanoimino)barbituric acid derivative] | [structure: same] |
| 124 | (214) | [structure: 2,4,6-triamino-5-methylpyrimidine] | [structure: same] |
| 125 | (215) | [structure: 2,6-dihydroxy-3-methyl-4-carboxypyridine] | [structure: same] |
| 126 | (216) | [structure: 1-phenyl-3-methyl-4-methyl-5-hydroxypyrazole] | [structure: same] |

TABLE 3-continued (20)

| Example Nr. | Compound Nr. | A'₁ | A'₂ |
|---|---|---|---|
| 127 | (217) | | |
| 128 | (218) | | |
| 129 | (219) | | |
| 130 | (220) | | |
| 131 | (221) | | |
| 132 | (222) | | |
| 133 | (223) | | |

TABLE 3-continued (20)

| Example Nr. | Compound Nr. | A'₁ | A'₂ |
| --- | --- | --- | --- |
| 134 | (224) | 2,4-substituted phenol with -OH and -CH₃ | acetoacetamide-N-(2-methyl-5-methoxy-4-sulfophenyl) |
| 135 | (225) | acetoacetamide-N-(4-sulfophenyl) | acetoacetamide-N-(4-sulfophenyl) |
| 136 | (226) | acetoacetamide-N-(3-sulfophenyl) | acetoacetamide-N-(4-sulfophenyl) |
| 137 | (227) | acetoacetamide-N-(2-methyl-5-methoxy-4-sulfophenyl) | acetoacetamide-N-(4-sulfophenyl) |
| 138 | (228) | 5-methylbarbituric acid | acetoacetamide-N-(4-sulfophenyl) |
| 139 | (229) | 5-methyl-2-cyanimino-barbituric acid derivative | acetoacetamide-N-(4-sulfophenyl) |
| 140 | (230) | 2,4,6-triamino-5-methylpyrimidine | acetoacetamide-N-(4-sulfophenyl) |

TABLE 3-continued (20)

| Example Nr. | Compound Nr. | A'₁ | A'₂ |
|---|---|---|---|
| 141 | (231) | 2,6-dihydroxy-3-methyl-4-carboxypyridine (HO₂C, OH, N, OH) | H₃C-C(O)-CH(CH₃)-C(O)-NH-C₆H₄-SO₃H |
| 142 | (232) | 1-phenyl-3-methyl-4-methyl-5-amino-pyrazole | H₃C-C(O)-CH(CH₃)-C(O)-NH-C₆H₄-SO₃H |
| 143 | (233) | 1-(3-sulfophenyl)-3-methyl-4-methyl-5-amino-pyrazole | H₃C-C(O)-CH(CH₃)-C(O)-NH-C₆H₄-SO₃H |
| 144 | (234) | 1-phenyl-3-methyl-4-methyl-5-hydroxy-pyrazole | H₃C-C(O)-CH(CH₃)-C(O)-NH-C₆H₄-SO₃H |
| 145 | (235) | 1-(4-sulfophenyl)-3-methyl-4-methyl-5-hydroxy-pyrazole | H₃C-C(O)-CH(CH₃)-C(O)-NH-C₆H₄-SO₃H |
| 146 | (236) | 2-hydroxy-5-methyl-benzoic acid | H₃C-C(O)-CH(CH₃)-C(O)-NH-C₆H₄-SO₃H |
| 147 | (237) | 2-hydroxy-3,5-dimethyl-benzoic acid | H₃C-C(O)-CH(CH₃)-C(O)-NH-C₆H₄-SO₃H |
| 148 | (238) | 2,4-dimethyl-6-hydroxyphenyl | H₃C-C(O)-CH(CH₃)-C(O)-NH-C₆H₄-SO₃H |

TABLE 3-continued
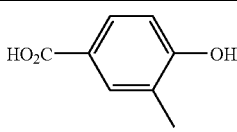
(20)
| Example Nr. | Compound Nr. | A'$_1$ | A'$_2$ |
|---|---|---|---|
| 149 | (239) | 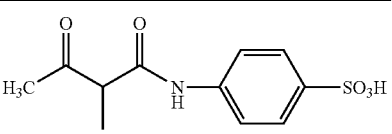 | 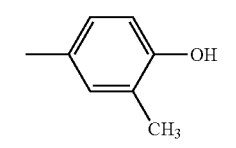 |
| 150 | (240) | 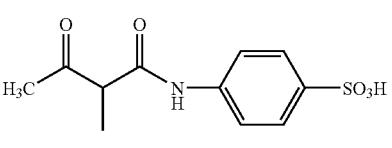 | 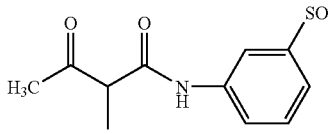 |
| 151 | (241) | 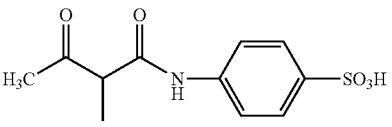 | 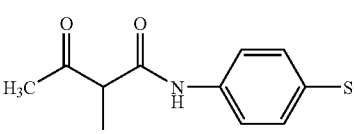 |
| 152 | (242) | 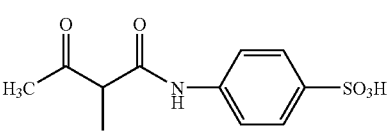 | 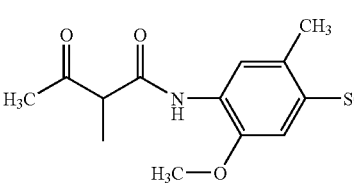 |
| 153 | (243) | 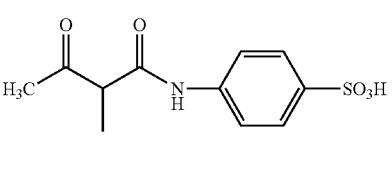 | 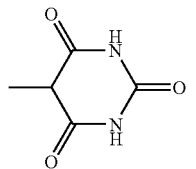 |
| 154 | (244) | 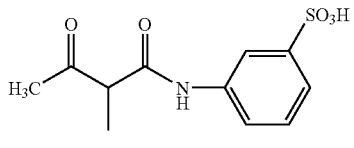 | 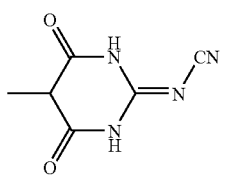 |
| 155 | (245) | 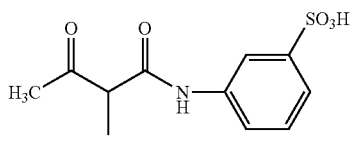 | 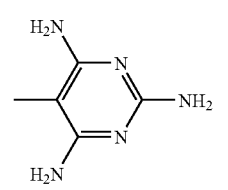 |
| 156 | (246) | 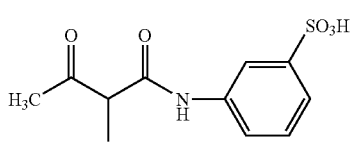 | |

TABLE 3-continued
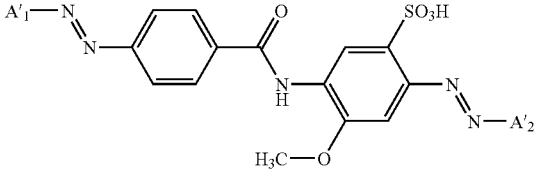
(20)
| Example Nr. | Compound Nr. | A'₁ | A'₂ |
|---|---|---|---|
| 157 | (247) | 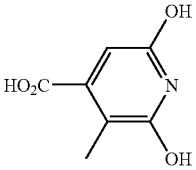 | 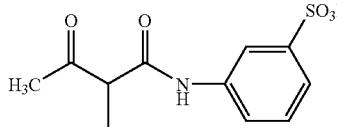 |
| 158 | (248) | 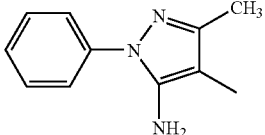 | 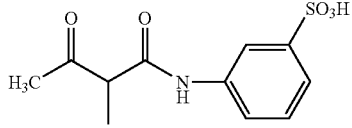 |
| 159 | (249) | 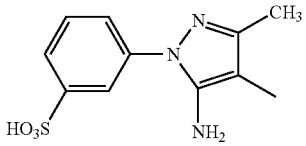 | 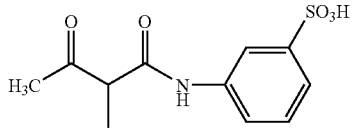 |
| 160 | (250) | 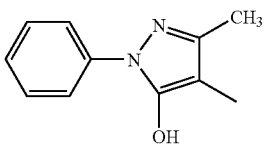 | 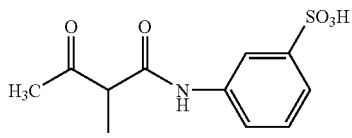 |
| 161 | (251) | 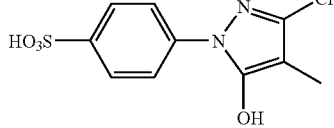 | 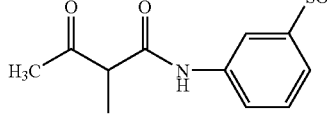 |
| 162 | (252) | 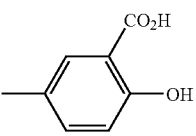 | 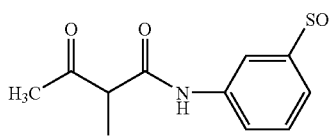 |
| 163 | (253) | 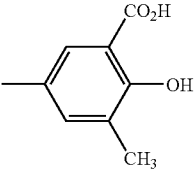 | 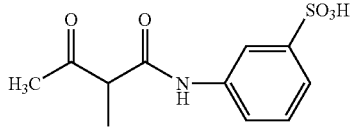 |
| 164 | (254) | 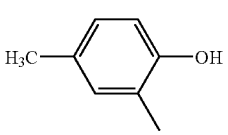 | 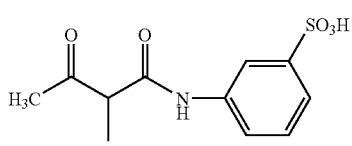 |

TABLE 3-continued (20)

| Example Nr. | Compound Nr. | A'₁ | A'₂ |
|---|---|---|---|
| 165 | (255) | 4-hydroxy-3-methyl-benzoic acid (HO₂C, OH, CH₃ substituents) | N-(3-sulfophenyl)-2-methyl-3-oxobutanamide |
| 166 | (256) | 2-hydroxy-3,5-dimethylphenyl (OH, 2× CH₃) | N-(3-sulfophenyl)-2-methyl-3-oxobutanamide |
| 167 | (257) | 5-amino-3,4-dimethyl-1-(3-sulfophenyl)-1H-pyrazole | 5-amino-3,4-dimethyl-1-(3-sulfophenyl)-1H-pyrazole |
| 168 | (258) | N-(3-sulfophenyl)-2-methyl-3-oxobutanamide | 5-amino-3,4-dimethyl-1-(3-sulfophenyl)-1H-pyrazole |
| 169 | (259) | N-(4-sulfophenyl)-2-methyl-3-oxobutanamide | 5-amino-3,4-dimethyl-1-(3-sulfophenyl)-1H-pyrazole |
| 170 | (260) | N-(2-methoxy-5-methyl-4-sulfophenyl)-2-methyl-3-oxobutanamide | 5-amino-3,4-dimethyl-1-(3-sulfophenyl)-1H-pyrazole |
| 171 | (261) | 5-methylbarbituric acid | 5-amino-3,4-dimethyl-1-(3-sulfophenyl)-1H-pyrazole |
| 172 | (262) | 2-(cyanoimino)-5-methyl-dihydropyrimidine-4,6(1H,5H)-dione | 5-amino-3,4-dimethyl-1-(3-sulfophenyl)-1H-pyrazole |

TABLE 3-continued
(20)
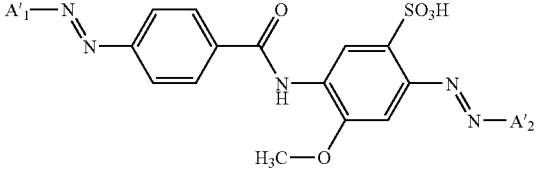
| Example Nr. | Compound Nr. | A'$_1$ | A'$_2$ |
|---|---|---|---|
| 173 | (263) | 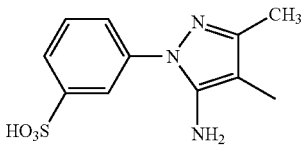 | 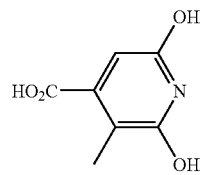 |
| 174 | (264) | 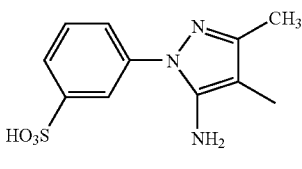 | 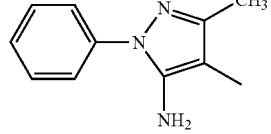 |
| 175 | (265) | 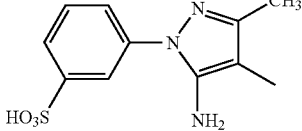 | 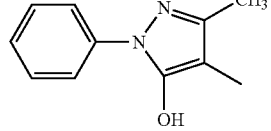 |
| 176 | (266) | 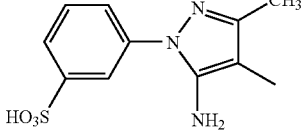 | 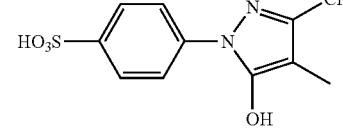 |
| 177 | (267) | 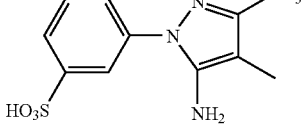 | 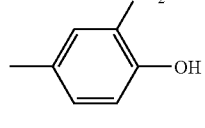 |
| 178 | (268) | 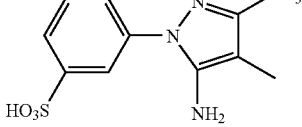 | 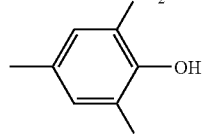 |
| 179 | (269) | 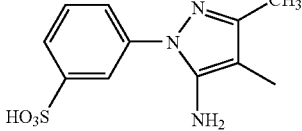 | 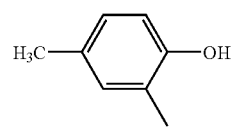 |
| 180 | (270) | 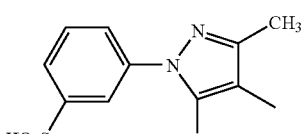 | |

TABLE 3-continued (20)

| Example Nr. | Compound Nr. | A'₁ | A'₂ |
|---|---|---|---|
| 181 | (271) | 3-methyl-4-hydroxy-5-carboxyphenyl (HO₂C, OH, CH₃ substituted phenyl) | 1-(3-sulfophenyl)-3-methyl-4-methyl-5-amino-pyrazole |
| 182 | (272) | 2-hydroxy-3-methyl-5-methylphenyl | 1-(3-sulfophenyl)-3-methyl-4-methyl-5-amino-pyrazole |
| 183 | (273) | 3-(2-methylacetoacetylamino)-phenyl-sulfonic acid (H₃C-CO-CH(CH₃)-CO-NH-C₆H₄-SO₃H) | 1-phenyl-3-methyl-4-methyl-5-amino-pyrazole |
| 184 | (274) | 4-(2-methylacetoacetylamino)-phenyl-sulfonic acid | 1-phenyl-3-methyl-4-methyl-5-amino-pyrazole |
| 185 | (275) | 1-(3-sulfophenyl)-3-methyl-4-methyl-5-amino-pyrazole | 1-phenyl-3-methyl-4-methyl-5-amino-pyrazole |
| 186 | (276) | 1-(4-sulfophenyl)-3-methyl-4-methyl-5-hydroxy-pyrazole | 1-phenyl-3-methyl-4-methyl-5-amino-pyrazole |
| 187 | (277) | 2-hydroxy-5-methyl-benzoic acid | 1-phenyl-3-methyl-4-methyl-5-amino-pyrazole |
| 188 | (278) | 2-hydroxy-3-methyl-5-methyl-benzoic acid | 1-phenyl-3-methyl-4-methyl-5-amino-pyrazole |

TABLE 3-continued (20)

| Example Nr. | Compound Nr. | A'₁ | A'₂ |
|---|---|---|---|
| 189 | (279) | 4-hydroxy-3,5-dimethylphenyl (H₃C—, —OH, —CH₃ substituents) | 1-phenyl-3-methyl-4-methyl-5-amino-pyrazole |
| 190 | (280) | 4-hydroxy-3-methyl-5-sulfophenyl (HO₃S—, —OH, —CH₃) | 1-phenyl-3-methyl-4-methyl-5-amino-pyrazole |
| 191 | (281) | acetoacetylamino-methyl-methoxy-sulfophenyl group | 1-phenyl-3-methyl-4-methyl-5-amino-pyrazole |

EXAMPLES 192-210

By proceeding in an analogous manner to that described in Examples 11-15, but replacing the compound of formula (100a) by the compound of formula (100c) and utilizing the appropriate coupling components, compounds of formula (21) are obtained, as summarized in the following Table 4.

TABLE 4

(21)

| Example Nr. | Compound Nr. | A'₁ | A'₂ |
|---|---|---|---|
| 192 | (282) | acetoacetylamino-methyl-methoxy-sulfophenyl group | acetoacetylamino-methyl-methoxy-sulfophenyl group |

TABLE 4-continued (21)

| Example Nr. | Compound Nr. | A'₁ | A'₂ |
|---|---|---|---|
| 193 | (283) | | |
| 194 | (284) | | |
| 195 | (285) | | |
| 196 | (286) | | |
| 197 | (287) | | |
| 198 | (288) | | |
| 199 | (289) | | |

TABLE 4-continued (21)

| Example Nr. | Compound Nr. | A'₁ | A'₂ |
|---|---|---|---|
| 200 | (290) | 1-phenyl-3-methyl-4-methyl-5-amino-pyrazole | |
| 201 | (291) | 1-phenyl-3-methyl-4-methyl-5-hydroxy-pyrazole | |
| 202 | (292) | 1-(4-sulfophenyl)-3-methyl-4-methyl-5-hydroxy-pyrazole | |
| 203 | (293) | 5-methyl-2-hydroxy-benzoic acid | |
| 204 | (294) | 3-methyl-5-methyl-2-hydroxy-benzoic acid | |
| 205 | (295) | 2,4-dimethyl-phenol | |
| 206 | (296) | 4-carboxy-2-methyl-phenol | |

TABLE 4-continued
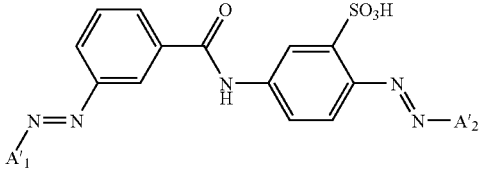
(21)
| Example Nr. | Compound Nr. | A'₁ | A'₂ |
|---|---|---|---|
| 207 | (297) | 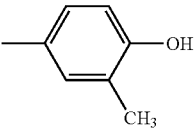 | 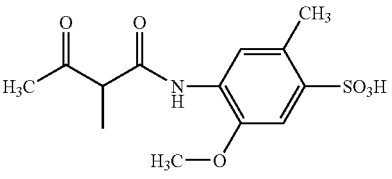 |
| 208 | (298) | 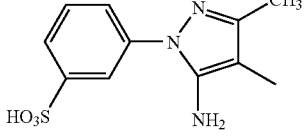 | 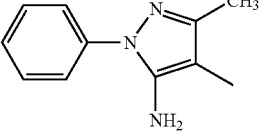 |
| 209 | (299) | 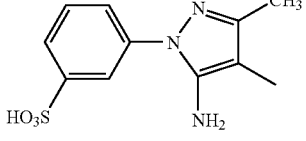 | 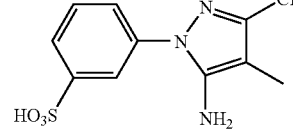 |
| 210 | (300) | 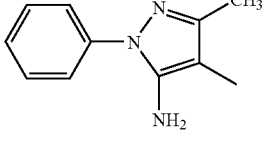 | 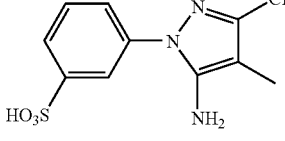 |
EXAMPLES 221-229
By proceeding in an analogous manner to that described in Examples 117-119, but replacing the compound of formula (100b) by the compound of formula (100d) and utilizing the appropriate coupling components, compounds of formula (22) are obtained, as summarized in the following Table 5
TABLE 5
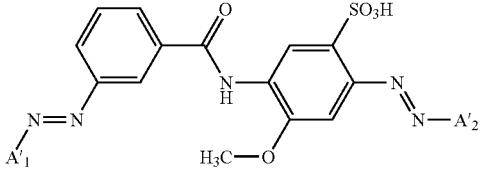
(22)
| Example Nr. | Compound Nr. | A'₁ | A'₂ |
|---|---|---|---|
| 211 | (301) | 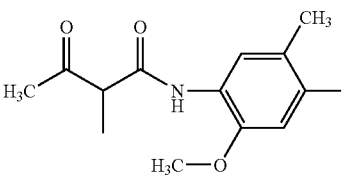 | 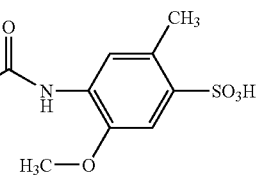 |

TABLE 5-continued
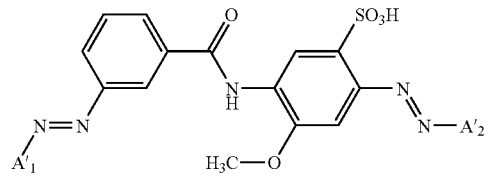
(22)
| Example Nr. | Compound Nr. | A'₁ | A'₂ |
|---|---|---|---|
| 212 | (302) | 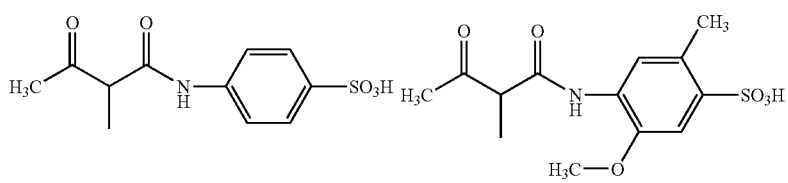 | |
| 213 | (303) | 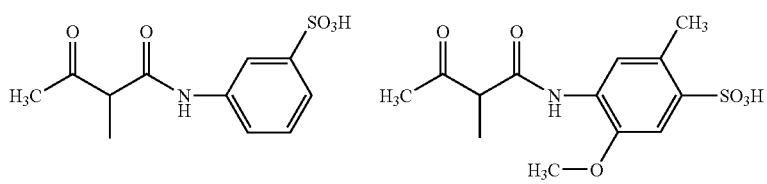 | |
| 214 | (304) | 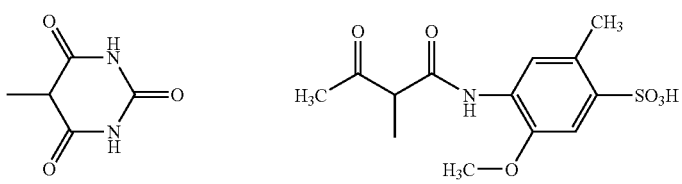 | |
| 215 | (305) | 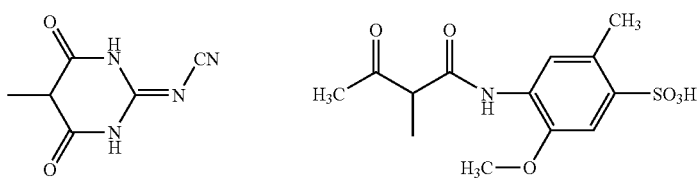 | |
| 216 | (306) | 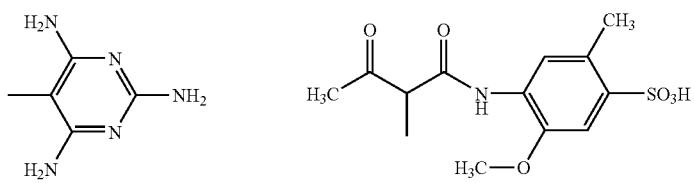 | |
| 217 | (307) | 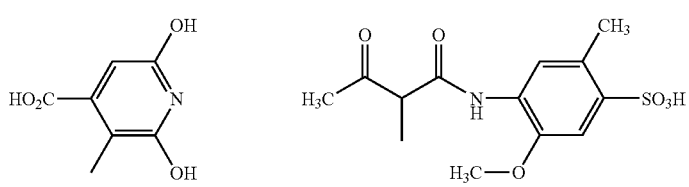 | |
| 218 | (308) | 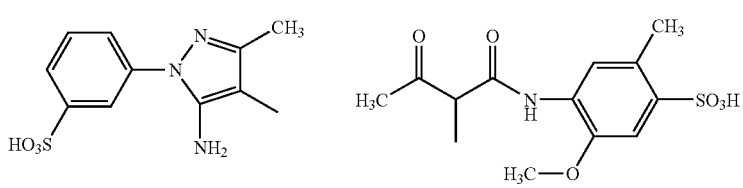 | |

TABLE 5-continued
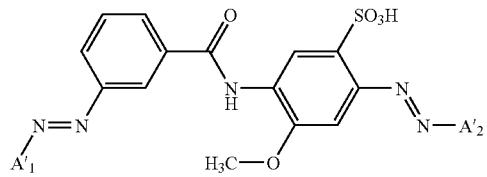
(22)
| Example Nr. | Compound Nr. | A'₁ | A'₂ |
|---|---|---|---|
| 219 | (309) | 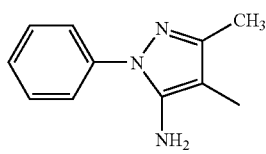 | 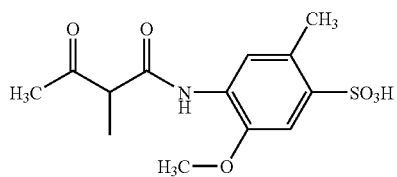 |
| 220 | (310) | 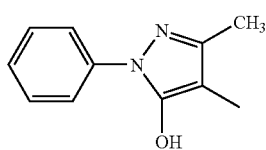 | 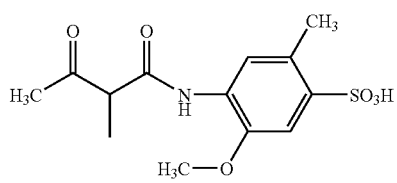 |
| 221 | (311) | 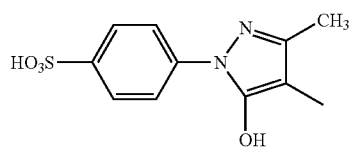 | 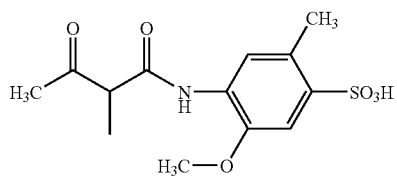 |
| 222 | (312) | 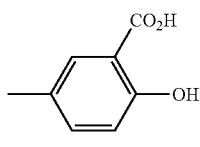 | 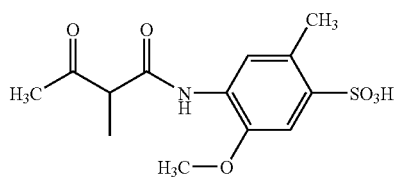 |
| 223 | (313) | 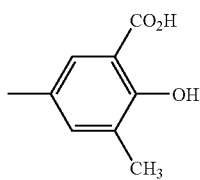 | 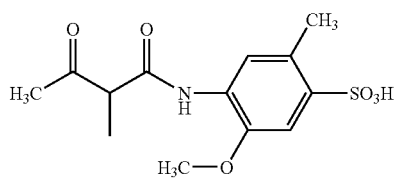 |
| 224 | (314) | 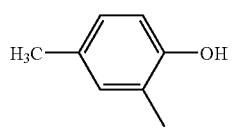 | 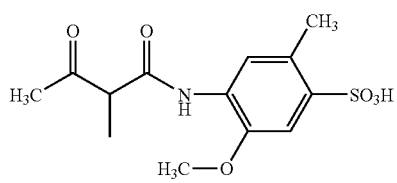 |
| 225 | (315) | 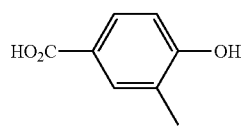 | 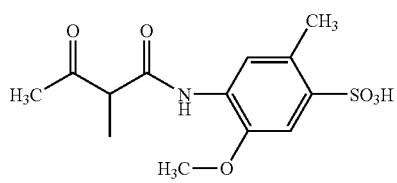 |

TABLE 5-continued
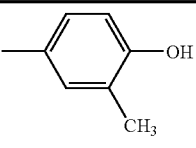
(22)
| Example Nr. | Compound Nr. | A'₁ | A'₂ |
| --- | --- | --- | --- |
| 226 | (316) | 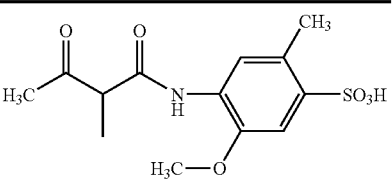 | 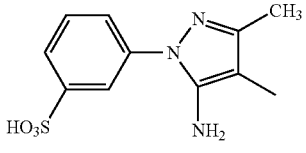 |
| 227 | (317) | 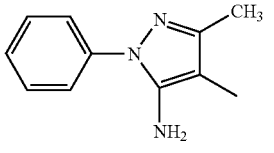 | 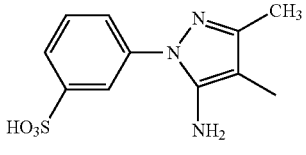 |
| 228 | (318) | 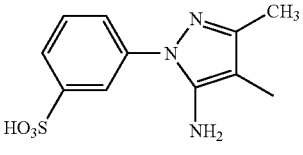 | 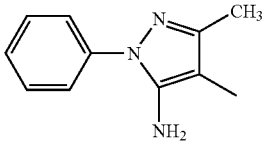 |
| 229 | (319) | 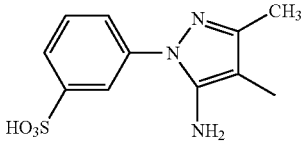 | 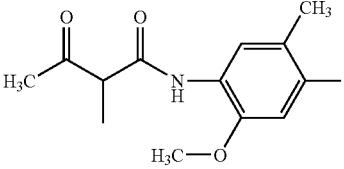 |
EXAMPLES 230-248
By proceeding in an analogous manner to that described in Examples 11-15, but replacing the compound of formula (100a) by the compound of formula (100e) and utilizing the appropriate coupling components, compounds of formula (23) are obtained, as summarized in the following Table 6.
TABLE 6
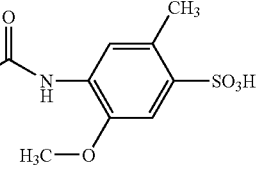
(23)
| Example Nr. | Compound Nr. | A'₁ | A'₂ |
| --- | --- | --- | --- |
| 230 | (320) | | |

TABLE 6-continued (23)

| Example Nr. | Compound Nr. | A'₁ | A'₂ |
|---|---|---|---|
| 231 | (321) | 3-methyl-3-oxo-N-(4-sulfophenyl)butanamide derivative | 2-methyl-3-oxo-N-(2-methoxy-4-methyl-5-sulfophenyl)butanamide |
| 232 | (322) | 2-methyl-3-oxo-N-(3-sulfophenyl)butanamide | 2-methyl-3-oxo-N-(2-methoxy-4-methyl-5-sulfophenyl)butanamide |
| 233 | (323) | 5-methylbarbituric acid | 2-methyl-3-oxo-N-(2-methoxy-4-methyl-5-sulfophenyl)butanamide |
| 234 | (324) | 2-cyanimino-5-methylbarbituric acid derivative | 2-methyl-3-oxo-N-(2-methoxy-4-methyl-5-sulfophenyl)butanamide |
| 235 | (325) | 2,4,6-triamino-5-methylpyrimidine | 2-methyl-3-oxo-N-(2-methoxy-4-methyl-5-sulfophenyl)butanamide |
| 236 | (326) | 2,6-dihydroxy-3-methylisonicotinic acid | 2-methyl-3-oxo-N-(2-methoxy-4-methyl-5-sulfophenyl)butanamide |
| 237 | (327) | 5-amino-3,4-dimethyl-1-(3-sulfophenyl)pyrazole | 2-methyl-3-oxo-N-(2-methoxy-4-methyl-5-sulfophenyl)butanamide |

TABLE 6-continued (23)

| Example Nr. | Compound Nr. | A'₁ | A'₂ |
| --- | --- | --- | --- |
| 238 | (328) | 5-amino-4-methyl-3-methyl-1-phenylpyrazole | 2-methyl-3-oxo-N-(2-methoxy-5-methyl-4-sulfophenyl)butanamide |
| 239 | (329) | 5-hydroxy-4-methyl-3-methyl-1-phenylpyrazole | 2-methyl-3-oxo-N-(2-methoxy-5-methyl-4-sulfophenyl)butanamide |
| 240 | (330) | 5-hydroxy-4-methyl-3-methyl-1-(4-sulfophenyl)pyrazole | 2-methyl-3-oxo-N-(2-methoxy-5-methyl-4-sulfophenyl)butanamide |
| 241 | (331) | 5-methyl-2-hydroxybenzoic acid | 2-methyl-3-oxo-N-(2-methoxy-5-methyl-4-sulfophenyl)butanamide |
| 242 | (332) | 3,5-dimethyl-2-hydroxybenzoic acid | 2-methyl-3-oxo-N-(2-methoxy-5-methyl-4-sulfophenyl)butanamide |
| 243 | (333) | 2,4-dimethylphenol | 2-methyl-3-oxo-N-(2-methoxy-5-methyl-4-sulfophenyl)butanamide |
| 244 | (334) | 3-methyl-4-hydroxybenzoic acid | 2-methyl-3-oxo-N-(2-methoxy-5-methyl-4-sulfophenyl)butanamide |

TABLE 6-continued
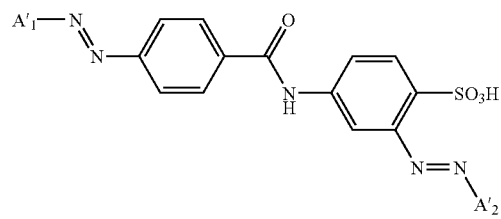
(23)
| Example Nr. | Compound Nr. | A'₁ | A'₂ |
|---|---|---|---|
| 245 | (335) | 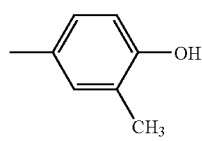 | 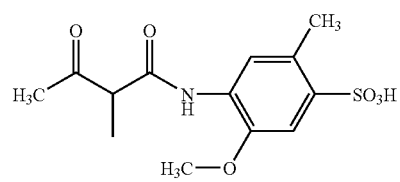 |
| 246 | (336) | 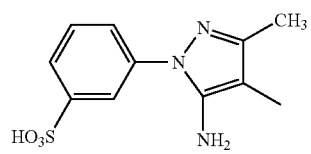 | 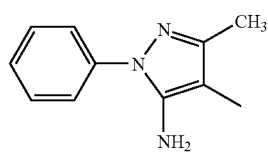 |
| 247 | (337) | 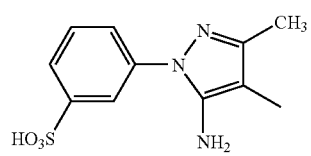 | 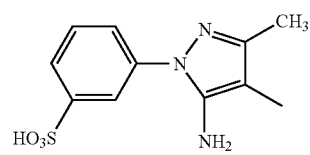 |
| 248 | (338) | 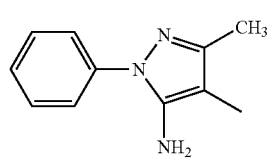 | 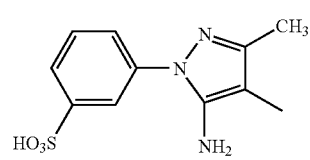 |

EXAMPLES 249-267
By proceeding in an analogous manner to that described in Examples 11-15, but replacing the compound of formula (100a) by the compound of formula (100f) and utilizing the appropriate coupling components, compounds of formula (24) are obtained, as summarized in the following Table 7.
TABLE 7
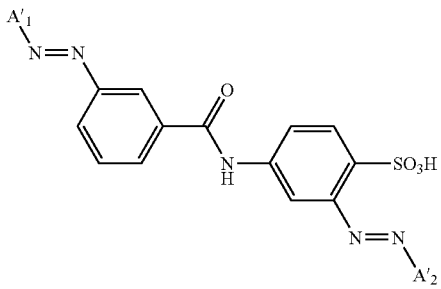
(24)
| Example Nr. | Compound Nr. | A'₁ | A'₂ |
|---|---|---|---|
| 249 | (339) | | |
| 250 | (340) | | |
| 251 | (341) | | |
| 252 | (342) | | |
| 253 | (343) | | |

TABLE 7-continued
(24)
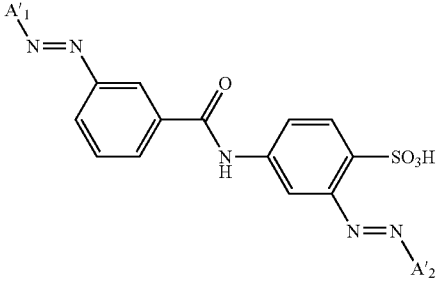
| Example Nr. | Compound Nr. | A'₁ | A'₂ |
|---|---|---|---|
| 254 | (344) | 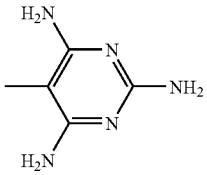 | 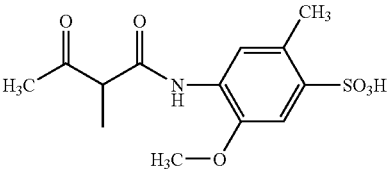 |
| 255 | (345) | 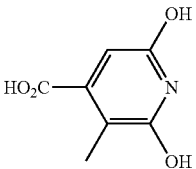 | 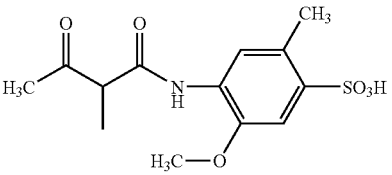 |
| 256 | (346) | 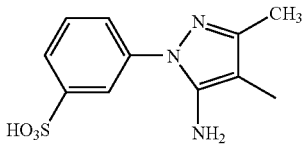 | 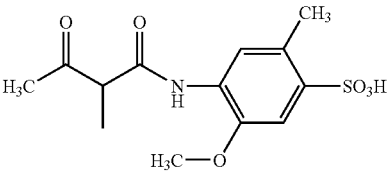 |
| 257 | (347) | 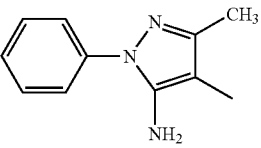 | 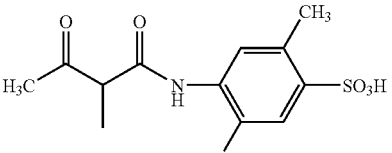 |
| 258 | (348) | 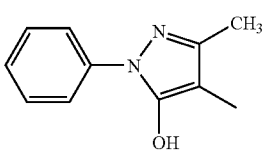 | 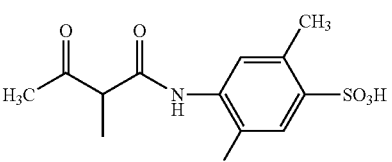 |
| 259 | (349) | 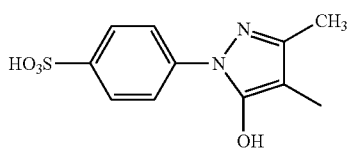 | 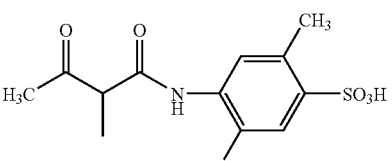 |

TABLE 7-continued (24)

| Example Nr. | Compound Nr. | A'₁ | A'₂ |
|---|---|---|---|
| 260 | (350) | 5-methyl-2-hydroxy-benzoic acid (CO₂H, OH) | 2-methyl-3-oxo-N-(5-methyl-2-methoxy-4-sulfophenyl)butanamide |
| 261 | (351) | 3-methyl-5-methyl-2-hydroxy-benzoic acid (CO₂H, OH, CH₃) | 2-methyl-3-oxo-N-(5-methyl-2-methoxy-4-sulfophenyl)butanamide |
| 262 | (352) | 2,4-dimethylphenol | 2-methyl-3-oxo-N-(5-methyl-2-methoxy-4-sulfophenyl)butanamide |
| 263 | (353) | 3-methyl-4-hydroxy-benzoic acid | 2-methyl-3-oxo-N-(5-methyl-2-methoxy-4-sulfophenyl)butanamide |
| 264 | (354) | 2,4-dimethylphenol | 2-methyl-3-oxo-N-(5-methyl-2-methoxy-4-sulfophenyl)butanamide |
| 265 | (355) | 5-amino-3,4-dimethyl-1-(3-sulfophenyl)pyrazole | 5-amino-3,4-dimethyl-1-phenyl-pyrazole |
| 266 | (356) | 5-amino-3,4-dimethyl-1-(3-sulfophenyl)pyrazole | 5-amino-3,4-dimethyl-1-(3-sulfophenyl)pyrazole |

TABLE 7-continued
(24)
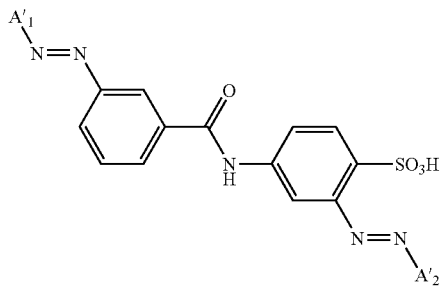
| Example Nr. | Compound Nr. | A'₁ | A'₂ |
|---|---|---|---|
| 267 | (357) | 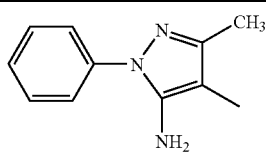 | 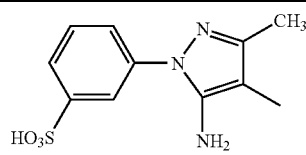 |
EXAMPLES 268-279
By proceeding in an analogous manner to that described in Examples 121-1, but replacing the compound of formula (100a) by the compound of formula (100g) and utilizing the appropriate coupling components, compounds of formula (25) are obtained, as summarized in the following Table 8.
TABLE 8
(25)
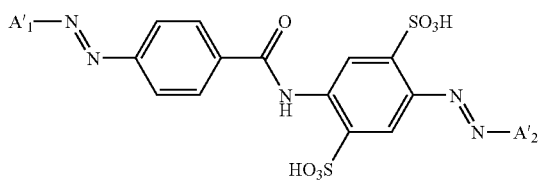
| Example Nr. | Compound Nr. | A'₁ | A'₂ |
|---|---|---|---|
| 268 | (358) | 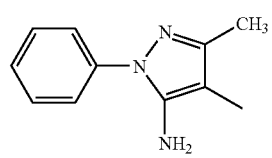 | 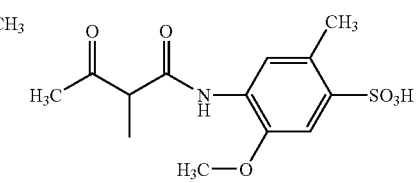 |
| 269 | (359) | 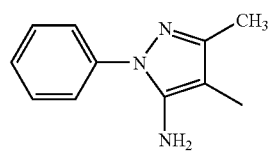 | 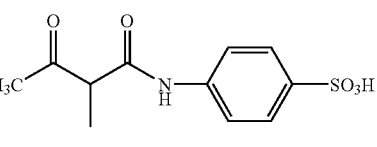 |
| 270 | (360) | 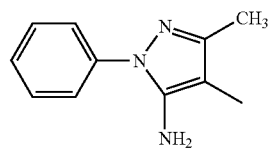 | 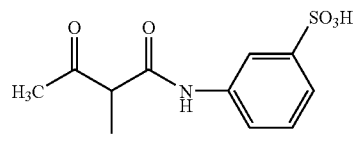 |

TABLE 8-continued
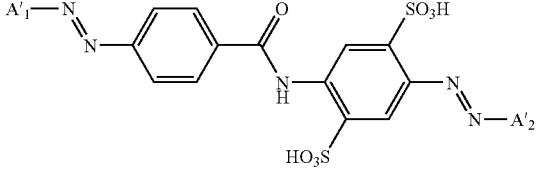
(25)
| Example Nr. | Compound Nr. | A'₁ | A'₂ |
|---|---|---|---|
| 271 | (361) | 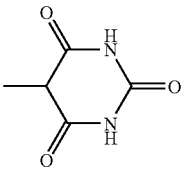 | 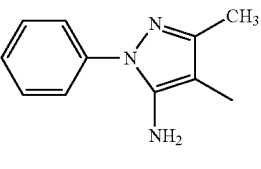 |
| 272 | (362) | 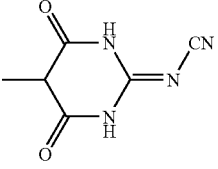 | 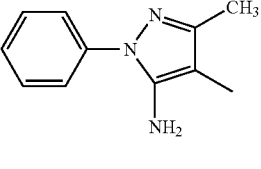 |
| 273 | (363) | 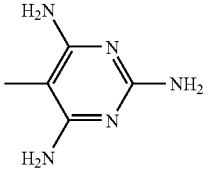 | 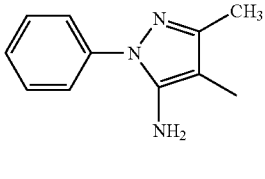 |
| 274 | (364) | 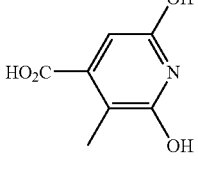 | 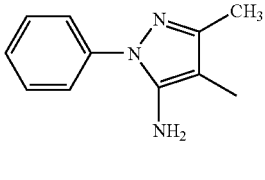 |
| 275 | (365) | 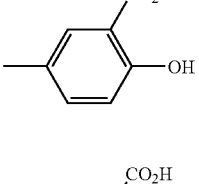 | 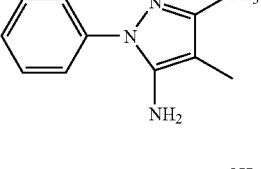 |
| 276 | (366) | 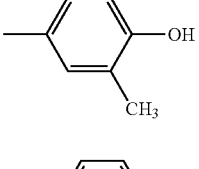 | 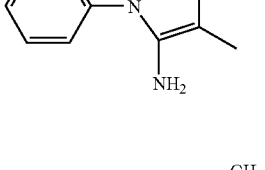 |
| 277 | (367) | 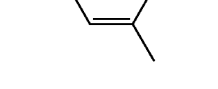 | 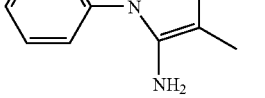 |

TABLE 8-continued (25)

| Example Nr. | Compound Nr. | A'₁ | A'₂ |
|---|---|---|---|
| 278 | (368) | HO₂C—⟨benzene⟩(CH₃)—OH | phenyl-pyrazole(CH₃)(CH₃)(NH₂) |
| 279 | (369) | CH₃—⟨benzene⟩(CH₃)—OH | phenyl-pyrazole(CH₃)(CH₃)(NH₂) |

EXAMPLES 280-291

By proceeding in an analogous manner to that described in Examples 11-15, but replacing the compound of formula (100a) by the compound of formula (100h) and utilizing the appropriate coupling components, compounds of formula (26) are obtained, as summarized in the following Table 9.

TABLE 9

(26)

| Example Nr. | Compound Nr. | A'₁ | A'₂ |
|---|---|---|---|
| 280 | (370) | phenyl-pyrazole(CH₃)(CH₃)(NH₂) | H₃C-CO-CH(CH₃)-C(O)NH—⟨benzene⟩(CH₃)(OCH₃)—SO₃H |
| 281 | (371) | phenyl-pyrazole(CH₃)(CH₃)(NH₂) | H₃C-CO-CH(CH₃)-C(O)NH—⟨benzene⟩—SO₃H |
| 282 | (372) | phenyl-pyrazole(CH₃)(CH₃)(NH₂) | H₃C-CO-CH(CH₃)-C(O)NH—⟨benzene⟩—SO₃H |

TABLE 9-continued (26)

| Example Nr. | Compound Nr. | A'₁ | A'₂ |
|---|---|---|---|
| 283 | (373) | 5-methylbarbituric acid | 5-amino-4-methyl-3-methyl-1-phenylpyrazole |
| 284 | (374) | 2-cyanoimino-5-methyl-4,6-dioxohexahydropyrimidine | 5-amino-4-methyl-3-methyl-1-phenylpyrazole |
| 285 | (375) | 2,4,6-triamino-5-methylpyrimidine | 5-amino-4-methyl-3-methyl-1-phenylpyrazole |
| 286 | (376) | 2,6-dihydroxy-3-methyl-isonicotinic acid | 5-amino-4-methyl-3-methyl-1-phenylpyrazole |
| 287 | (377) | 5-methylsalicylic acid | 5-amino-4-methyl-3-methyl-1-phenylpyrazole |
| 288 | (378) | 3,5-dimethylsalicylic acid | 5-amino-4-methyl-3-methyl-1-phenylpyrazole |
| 289 | (379) | 2,4-dimethylphenol | 5-amino-4-methyl-3-methyl-1-phenylpyrazole |

TABLE 9-continued (26)

| Example Nr. | Compound Nr. | $A'_1$ | $A'_2$ |
|---|---|---|---|
| 290 | (380) | HO₂C—⟨ ⟩—OH with CH₃ | 1-phenyl-3-methyl-4-methyl-5-amino pyrazole |
| 291 | (381) | methyl-⟨ ⟩—OH with CH₃ | 1-phenyl-3-methyl-4-methyl-5-amino pyrazole |

EXAMPLES 292-362

By proceeding in an analogous manner to that described in Examples 11-15, but replacing the compound of formula (100a) by the compound of formula (100i) and utilizing the appropriate coupling components, compounds of formula (27) are obtained, as summarized in the following Table 10.

TABLE 10

(27)

| Example Nr. | Compound Nr. | $A'_1$ | $A'_2$ |
|---|---|---|---|
| 292 | (382) | H₃C-CO-CH(CH₃)-CO-NH-C₆H₄-SO₃H | H₃C-CO-CH(CH₃)-CO-NH-(2-CH₃, 5-OCH₃, 4-SO₃H-phenyl) |
| 293 | (383) | H₃C-CO-CH(CH₃)-CO-NH-(3-SO₃H-phenyl) | H₃C-CO-CH(CH₃)-CO-NH-(2-CH₃, 5-OCH₃, 4-SO₃H-phenyl) |

TABLE 10-continued (27)

| Example Nr. | Compound Nr. | A'₁ | A'₂ |
| --- | --- | --- | --- |
| 294 | (384) | 5-methylbarbituric acid | 2-methyl-3-oxo-N-(4-sulfo-2-methoxy-5-methylphenyl)butanamide |
| 295 | (385) | 2-cyanoimino-5-methylbarbituric acid | 2-methyl-3-oxo-N-(4-sulfo-2-methoxy-5-methylphenyl)butanamide |
| 296 | (386) | 2,4,6-triamino-5-methylpyrimidine | 2-methyl-3-oxo-N-(4-sulfo-2-methoxy-5-methylphenyl)butanamide |
| 297 | (387) | 2,6-dihydroxy-3-methylpyridine-4-carboxylic acid | 2-methyl-3-oxo-N-(4-sulfo-2-methoxy-5-methylphenyl)butanamide |
| 298 | (388) | 3,4-dimethyl-1-phenyl-5-hydroxypyrazole | 2-methyl-3-oxo-N-(4-sulfo-2-methoxy-5-methylphenyl)butanamide |
| 299 | (389) | 3,4-dimethyl-1-(4-sulfophenyl)-5-hydroxypyrazole | 2-methyl-3-oxo-N-(4-sulfo-2-methoxy-5-methylphenyl)butanamide |
| 300 | (390) | 4-methyl-5-hydroxy-1-(4-sulfophenyl)pyrazole-3-carboxylic acid | 2-methyl-3-oxo-N-(4-sulfo-2-methoxy-5-methylphenyl)butanamide |

TABLE 10-continued (27)

| Example Nr. | Compound Nr. | A'₁ | A'₂ |
|---|---|---|---|
| 301 | (391) | 3-carboxy-4-methyl-5-hydroxy-1-phenylpyrazole | 2-methyl-3-oxo-N-(2-methoxy-5-methyl-4-sulfophenyl)butanamide |
| 302 | (392) | 5-methyl-2-hydroxybenzoic acid | 2-methyl-3-oxo-N-(2-methoxy-5-methyl-4-sulfophenyl)butanamide |
| 303 | (393) | 3-methyl-5-methyl-2-hydroxybenzoic acid | 2-methyl-3-oxo-N-(2-methoxy-5-methyl-4-sulfophenyl)butanamide |
| 304 | (394) | 2,4-dimethylphenol | 2-methyl-3-oxo-N-(2-methoxy-5-methyl-4-sulfophenyl)butanamide |
| 305 | (395) | 3-methyl-4-hydroxybenzoic acid | 2-methyl-3-oxo-N-(2-methoxy-5-methyl-4-sulfophenyl)butanamide |
| 306 | (396) | 2,4-dimethylphenol | 2-methyl-3-oxo-N-(2-methoxy-5-methyl-4-sulfophenyl)butanamide |
| 307 | (397) | 2-methyl-3-oxo-N-(4-sulfophenyl)butanamide | 2-methyl-3-oxo-N-(4-sulfophenyl)butanamide |
| 308 | (398) | 2-methyl-3-oxo-N-(3-sulfophenyl)butanamide | 2-methyl-3-oxo-N-(4-sulfophenyl)butanamide |

TABLE 10-continued
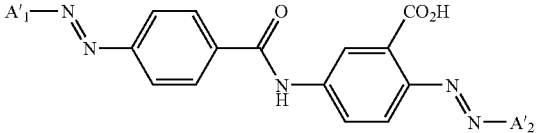
(27)
| Example Nr. | Compound Nr. | A'$_1$ | A'$_2$ |
|---|---|---|---|
| 309 | (399) | 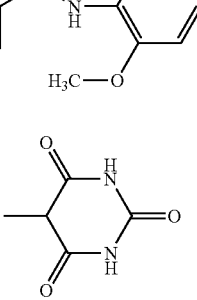 | 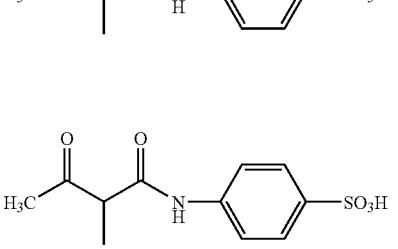 |
| 310 | (400) | 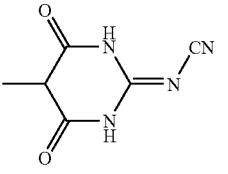 | 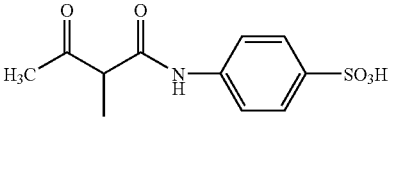 |
| 311 | (401) | 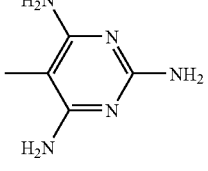 | 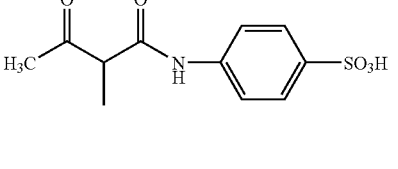 |
| 312 | (402) | 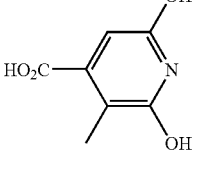 | 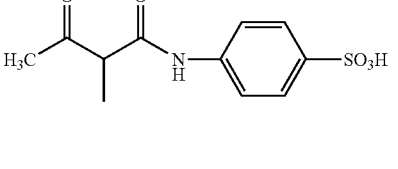 |
| 313 | (403) | 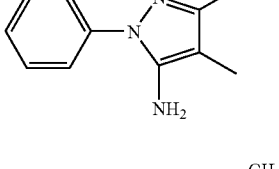 | 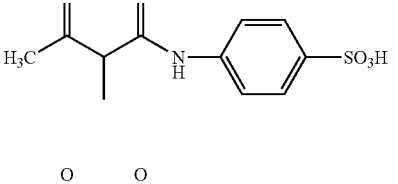 |
| 314 | (404) | 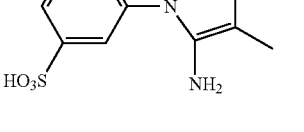 | |
| 315 | (405) | 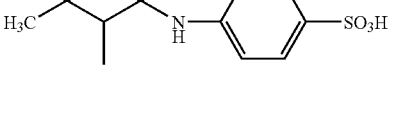 | |

TABLE 10-continued
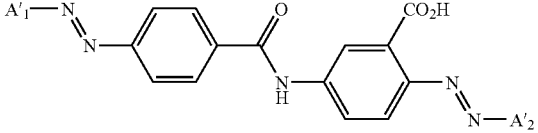
(27)
| Example Nr. | Compound Nr. | A'$_1$ | A'$_2$ |
|---|---|---|---|
| 316 | (406) | 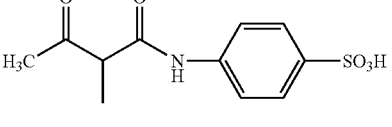 | 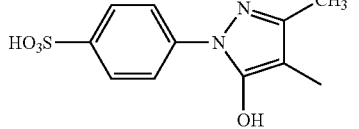 |
| 317 | (407) | 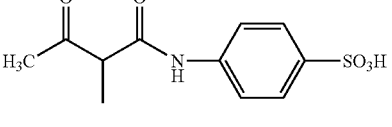 | 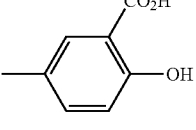 |
| 318 | (408) | 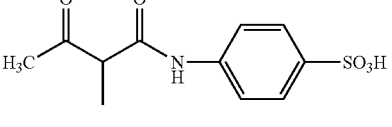 | 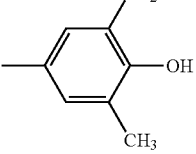 |
| 319 | (409) | 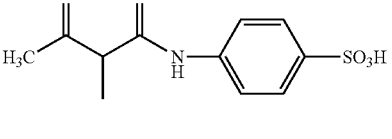 | 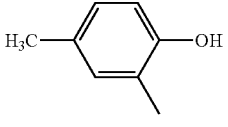 |
| 320 | (410) | 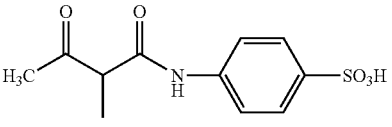 | 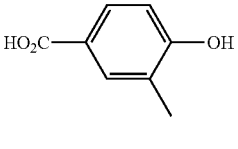 |
| 321 | (411) | 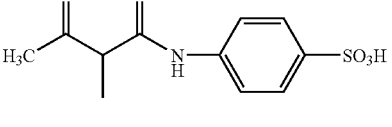 | 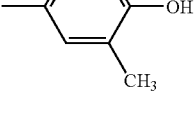 |
| 322 | (412) | 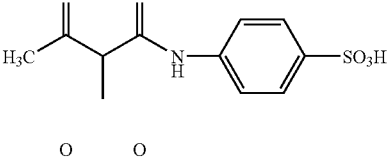 | 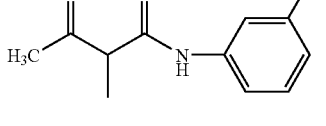 |
| 323 | (413) | 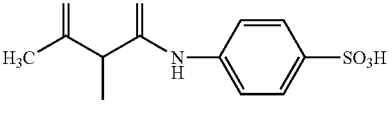 | 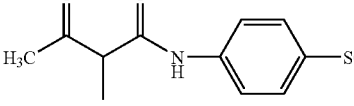 |
| 324 | (414) | 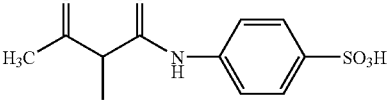 | |

TABLE 10-continued (27)

| Example Nr. | Compound Nr. | A'₁ | A'₂ |
|---|---|---|---|
| 325 | (415) | [structure] | [structure] |
| 326 | (416) | [structure] | [structure] |
| 327 | (417) | [structure] | [structure] |
| 328 | (418) | [structure] | [structure] |
| 329 | (419) | [structure] | [structure] |
| 330 | (420) | [structure] | [structure] |
| 331 | (421) | [structure] | [structure] |
| 332 | (422) | [structure] | [structure] |

TABLE 10-continued (27)

| Example Nr. | Compound Nr. | A'₁ | A'₂ |
|---|---|---|---|
| 333 | (423) | 1-(4-sulfophenyl)-3-methyl-4-methyl-5-hydroxypyrazole | 2-methyl-3-oxo-N-(3-sulfophenyl)butanamide |
| 334 | (424) | 5-methyl-2-hydroxybenzoic acid | 2-methyl-3-oxo-N-(3-sulfophenyl)butanamide |
| 335 | (425) | 3,5-dimethyl-2-hydroxybenzoic acid | 2-methyl-3-oxo-N-(3-sulfophenyl)butanamide |
| 336 | (426) | 2,4-dimethylphenol | 2-methyl-3-oxo-N-(3-sulfophenyl)butanamide |
| 337 | (427) | 4-hydroxy-3-methylbenzoic acid | 2-methyl-3-oxo-N-(3-sulfophenyl)butanamide |
| 338 | (428) | 2,4-dimethylphenol (isomer) | 2-methyl-3-oxo-N-(3-sulfophenyl)butanamide |
| 339 | (429) | 1-(3-sulfophenyl)-3-methyl-4-methyl-5-aminopyrazole | 1-(3-sulfophenyl)-3-methyl-4-methyl-5-aminopyrazole |
| 340 | (430) | 2-methyl-3-oxo-N-(3-sulfophenyl)butanamide | 1-(3-sulfophenyl)-3-methyl-4-methyl-5-aminopyrazole |

TABLE 10-continued (27)

| Example Nr. | Compound Nr. | A'₁ | A'₂ |
|---|---|---|---|
| 341 | (431) | 2-methyl-3-oxo-N-(4-sulfophenyl)butanamide group | 3-(5-amino-3,4-dimethylpyrazol-1-yl)benzenesulfonic acid group |
| 342 | (432) | 2-methyl-3-oxo-N-(2-methyl-5-methoxy-4-sulfophenyl)butanamide group | 3-(5-amino-3,4-dimethylpyrazol-1-yl)benzenesulfonic acid group |
| 343 | (433) | 5-methylbarbituric acid group | 3-(5-amino-3,4-dimethylpyrazol-1-yl)benzenesulfonic acid group |
| 344 | (434) | 2-cyanimino-5-methyl-4,6-dioxohexahydropyrimidine group | 3-(5-amino-3,4-dimethylpyrazol-1-yl)benzenesulfonic acid group |
| 345 | (435) | 2,4,6-triamino-5-methylpyrimidine group | 3-(5-amino-3,4-dimethylpyrazol-1-yl)benzenesulfonic acid group |
| 346 | (436) | 2,6-dihydroxy-5-methylpyridine-4-carboxylic acid group | 3-(5-amino-3,4-dimethylpyrazol-1-yl)benzenesulfonic acid group |
| 347 | (437) | 5-amino-3,4-dimethyl-1-phenylpyrazole group | 3-(5-amino-3,4-dimethylpyrazol-1-yl)benzenesulfonic acid group |
| 348 | (438) | 5-hydroxy-3,4-dimethyl-1-phenylpyrazole group | 3-(5-amino-3,4-dimethylpyrazol-1-yl)benzenesulfonic acid group |

TABLE 10-continued (27)

| Example Nr. | Compound Nr. | A'₁ | A'₂ |
|---|---|---|---|
| 349 | (439) | | |
| 350 | (440) | | |
| 351 | (441) | | |
| 352 | (442) | | |
| 353 | (443) | | |
| 354 | (444) | | |
| 355 | (445) | | |
| 356 | (446) | | |

TABLE 10-continued (27)

| Example Nr. | Compound Nr. | A'₁ | A'₂ |
|---|---|---|---|
| 357 | (447) | 3-sulfophenyl-pyrazole (3-CH₃, 4-CH₃, 5-NH₂) | 1-phenyl-pyrazole (3-CH₃, 4-CH₃, 5-NH₂) |
| 358 | (448) | 4-sulfophenyl-pyrazole (3-CH₃, 4-CH₃, 5-OH) | 1-phenyl-pyrazole (3-CH₃, 4-CH₃, 5-NH₂) |
| 359 | (449) | 5-methyl-2-hydroxy-benzoic acid | 1-phenyl-pyrazole (3-CH₃, 4-CH₃, 5-NH₂) |
| 360 | (450) | 3,5-dimethyl-2-hydroxy-benzoic acid | 1-phenyl-pyrazole (3-CH₃, 4-CH₃, 5-NH₂) |
| 361 | (451) | 4-hydroxy-3-methyl-benzoic acid | 1-phenyl-pyrazole (3-CH₃, 4-CH₃, 5-NH₂) |
| 362 | (452) | 4-sulfo-2-methyl-phenol | 1-phenyl-pyrazole (3-CH₃, 4-CH₃, 5-NH₂) |

EXAMPLES 363-433

By proceeding in an analogous manner to that described in Examples 11-15, but replacing the compound of formula (100a) by the compound of formula (100J) and utilizing the appropriate coupling components, compounds of formula (28) are obtained, as summarized in the following Table 11.

TABLE 11

(28)

| Example Nr. | Compound Nr. | A'₁ | A'₂ |
|---|---|---|---|
| 363 | (453) | | |
| 364 | (454) | | |
| 365 | (455) | | |
| 366 | (456) | | |
| 367 | (457) | | |
| 368 | (458) | | |

TABLE 11-continued
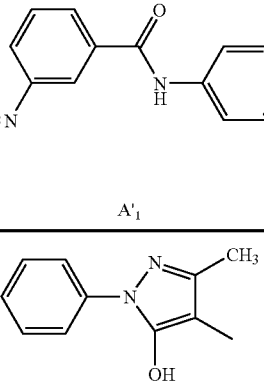
(28)
| Example Nr. | Compound Nr. | A'₁ | A'₂ |
|---|---|---|---|
| 369 | (459) | 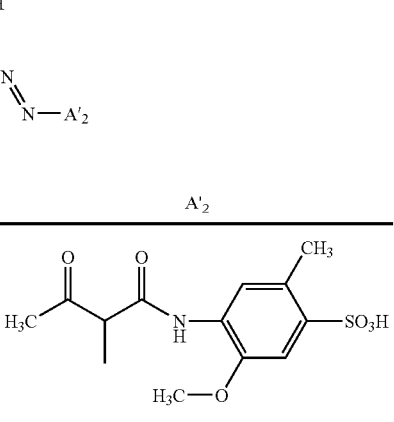 | 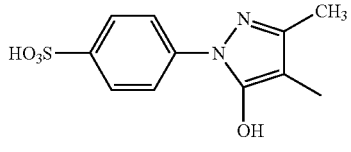 |
| 370 | (460) | 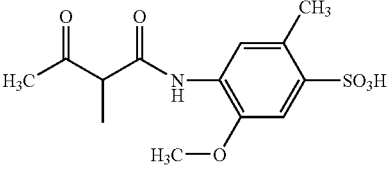 | 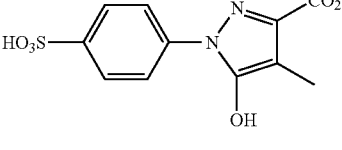 |
| 371 | (461) | 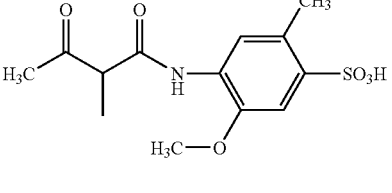 | 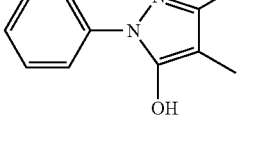 |
| 372 | (462) | 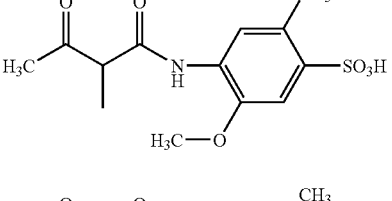 | 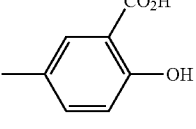 |
| 373 | (463) | 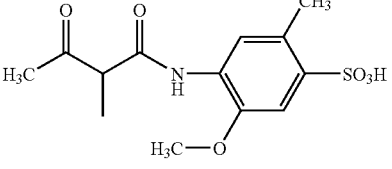 | 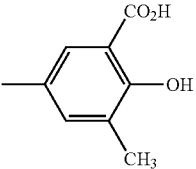 |
| 374 | (464) | 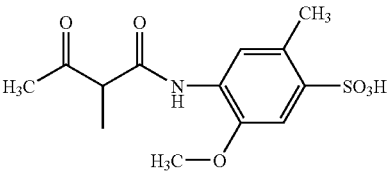 | 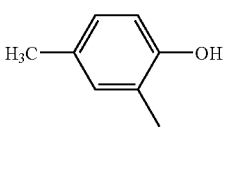 |
| 375 | (465) | 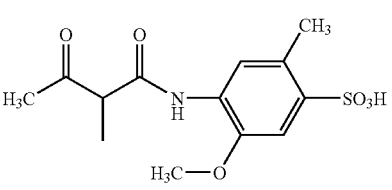 | |

TABLE 11-continued (28)

| Example Nr. | Compound Nr. | A'₁ | A'₂ |
|---|---|---|---|
| 376 | (466) | HO₂C–C₆H₂(CH₃)–OH (4-hydroxy-3-methylbenzoic acid) | H₃C–C(O)–CH(CH₃)–C(O)–NH–C₆H₂(CH₃)(OCH₃)–SO₃H |
| 377 | (467) | 2,4-dimethylphenol (CH₃, CH₃, OH) | H₃C–C(O)–CH(CH₃)–C(O)–NH–C₆H₂(CH₃)(OCH₃)–SO₃H |
| 378 | (468) | H₃C–C(O)–CH(CH₃)–C(O)–NH–C₆H₄–SO₃H | H₃C–C(O)–CH(CH₃)–C(O)–NH–C₆H₄–SO₃H |
| 379 | (469) | H₃C–C(O)–CH(CH₃)–C(O)–NH–C₆H₄–SO₃H (meta) | H₃C–C(O)–CH(CH₃)–C(O)–NH–C₆H₄–SO₃H |
| 380 | (470) | H₃C–C(O)–CH(CH₃)–C(O)–NH–C₆H₂(CH₃)(OCH₃)–SO₃H | H₃C–C(O)–CH(CH₃)–C(O)–NH–C₆H₄–SO₃H |
| 381 | (471) | 5-methylbarbituric acid | H₃C–C(O)–CH(CH₃)–C(O)–NH–C₆H₄–SO₃H |
| 382 | (472) | 2-(cyanoimino)-5-methyl-barbituric-like | H₃C–C(O)–CH(CH₃)–C(O)–NH–C₆H₄–SO₃H |

TABLE 11-continued (28)

| Example Nr. | Compound Nr. | A'₁ | A'₂ |
|---|---|---|---|
| 383 | (473) | 2,4,6-triamino-5-methylpyrimidine | 2-methyl-3-oxo-N-(4-sulfophenyl)butanamide |
| 384 | (474) | 4-carboxy-2,6-dihydroxy-3-methylpyridine | 2-methyl-3-oxo-N-(4-sulfophenyl)butanamide |
| 385 | (475) | 5-amino-3,4-dimethyl-1-phenylpyrazole | 2-methyl-3-oxo-N-(4-sulfophenyl)butanamide |
| 386 | (476) | 5-amino-3,4-dimethyl-1-(3-sulfophenyl)pyrazole | 2-methyl-3-oxo-N-(4-sulfophenyl)butanamide |
| 387 | (477) | 3,4-dimethyl-5-hydroxy-1-phenylpyrazole | 2-methyl-3-oxo-N-(4-sulfophenyl)butanamide |
| 388 | (478) | 3,4-dimethyl-5-hydroxy-1-(4-sulfophenyl)pyrazole | 2-methyl-3-oxo-N-(4-sulfophenyl)butanamide |
| 389 | (479) | 2-hydroxy-5-methylbenzoic acid | 2-methyl-3-oxo-N-(4-sulfophenyl)butanamide |
| 390 | (480) | 2-hydroxy-3,5-dimethylbenzoic acid | 2-methyl-3-oxo-N-(4-sulfophenyl)butanamide |

TABLE 11-continued (28)

| Example Nr. | Compound Nr. | A'₁ | A'₂ |
|---|---|---|---|
| 391 | (481) | 2,4-dimethylphenol | 2-(4-sulfophenylcarbamoyl)propan-1-one (methyl) |
| 392 | (482) | 4-hydroxy-3-methylbenzoic acid | 2-(4-sulfophenylcarbamoyl)propan-1-one (methyl) |
| 393 | (483) | 2,4-dimethylphenol | 2-(4-sulfophenylcarbamoyl)propan-1-one (methyl) |
| 394 | (484) | 2-(3-sulfophenylcarbamoyl)propan-1-one (methyl) | 2-(4-sulfophenylcarbamoyl)propan-1-one (methyl) |
| 395 | (485) | 2-(4-sulfophenylcarbamoyl)propan-1-one (methyl) | 2-(4-sulfophenylcarbamoyl)propan-1-one (methyl) |
| 396 | (486) | 2-(2-methyl-5-methoxy-4-sulfophenylcarbamoyl)propan-1-one | 2-(4-sulfophenylcarbamoyl)propan-1-one (methyl) |
| 397 | (487) | 5-methylbarbituric acid | 2-(3-sulfophenylcarbamoyl)propan-1-one (methyl) |
| 398 | (488) | 2-cyanimino-5-methylbarbituric acid derivative | 2-(3-sulfophenylcarbamoyl)propan-1-one (methyl) |

TABLE 11-continued
(28)
| Example Nr. | Compound Nr. | A'₁ | A'₂ |
|---|---|---|---|
| 399 | (489) | 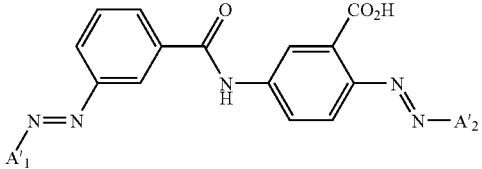 | 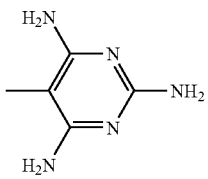 |
| 400 | (490) | 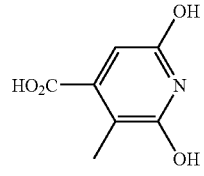 | |
| 401 | (491) | 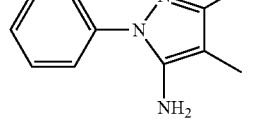 | |
| 402 | (492) | 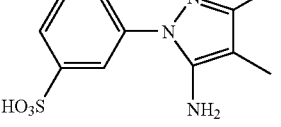 | |
| 3403 | (493) | 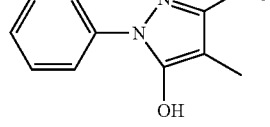 | |
| 404 | (494) | 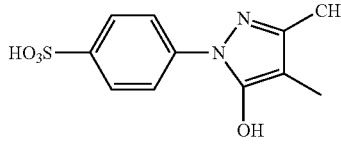 | |
| 405 | (495) | 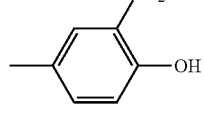 | |
| 406 | (496) | 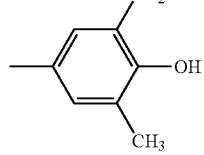 | |

TABLE 11-continued (28)

| Example Nr. | Compound Nr. | A'₁ | A'₂ |
| --- | --- | --- | --- |
| 407 | (497) | 4-hydroxy-2,5-dimethylphenyl | 3-(2-methylacetoacetamido)benzenesulfonic acid |
| 408 | (498) | 4-hydroxy-3-methyl-5-carboxyphenyl | 3-(2-methylacetoacetamido)benzenesulfonic acid |
| 409 | (499) | 4-hydroxy-2,5-dimethylphenyl | 3-(2-methylacetoacetamido)benzenesulfonic acid |
| 410 | (500) | 5-amino-3,4-dimethyl-1-(3-sulfophenyl)pyrazole | 5-amino-3,4-dimethyl-1-(3-sulfophenyl)pyrazole |
| 411 | (501) | 3-(2-methylacetoacetamido)benzenesulfonic acid | 5-amino-3,4-dimethyl-1-(3-sulfophenyl)pyrazole |
| 412 | (502) | 4-(2-methylacetoacetamido)benzenesulfonic acid | 5-amino-3,4-dimethyl-1-(3-sulfophenyl)pyrazole |
| 413 | (503) | 4-(2-methylacetoacetamido)-2-methyl-5-methoxybenzenesulfonic acid | 5-amino-3,4-dimethyl-1-(3-sulfophenyl)pyrazole |
| 414 | (504) | 5-methylbarbituric acid | 5-amino-3,4-dimethyl-1-(3-sulfophenyl)pyrazole |

TABLE 11-continued (28)

| Example Nr. | Compound Nr. | A'₁ | A'₂ |
|---|---|---|---|
| 415 | (505) | 5-methyl-2-(cyanoimino)-pyrimidine-4,6(1H,5H)-dione | 3-methyl-4-methyl-5-amino-1-(3-sulfophenyl)pyrazole |
| 416 | (506) | 2,4,6-triamino-5-methylpyrimidine | 3-methyl-4-methyl-5-amino-1-(3-sulfophenyl)pyrazole |
| 417 | (507) | 2,6-dihydroxy-3-methyl-isonicotinic acid | 3-methyl-4-methyl-5-amino-1-(3-sulfophenyl)pyrazole |
| 418 | (508) | 3-methyl-4-methyl-5-amino-1-phenylpyrazole | 3-methyl-4-methyl-5-amino-1-(3-sulfophenyl)pyrazole |
| 419 | (509) | 3-methyl-4-methyl-5-hydroxy-1-phenylpyrazole | 3-methyl-4-methyl-5-amino-1-(3-sulfophenyl)pyrazole |
| 420 | (510) | 3-methyl-4-methyl-5-hydroxy-1-(4-sulfophenyl)pyrazole | 3-methyl-4-methyl-5-amino-1-(3-sulfophenyl)pyrazole |
| 421 | (511) | 5-methyl-2-hydroxy-benzoic acid | 3-methyl-4-methyl-5-amino-1-(3-sulfophenyl)pyrazole |
| 422 | (512) | 3-methyl-5-methyl-2-hydroxy-benzoic acid | 3-methyl-4-methyl-5-amino-1-(3-sulfophenyl)pyrazole |

TABLE 11-continued
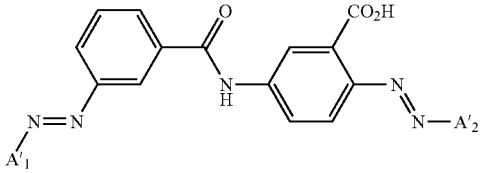
(28)
| Example Nr. | Compound Nr. | A'₁ | A'₂ |
|---|---|---|---|
| 423 | (513) | 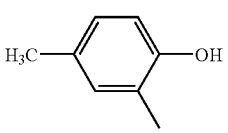 | 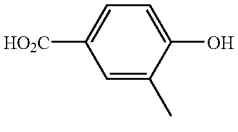 |
| 424 | (514) | 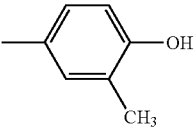 | 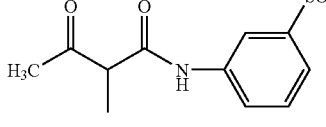 |
| 425 | (515) | 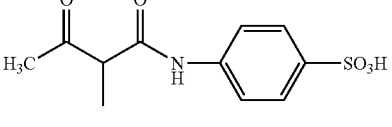 | 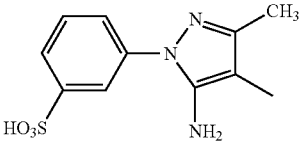 |
| 426 | (516) | 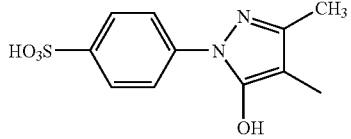 | 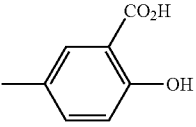 |
| 427 | (517) | | |
| 428 | (518) | | |
| 429 | (519) | | |
| 430 | (520) | | |

TABLE 11-continued (Structure 28): A diazo compound with central benzamide core; left phenyl bears CO-NH linkage and meta-N=N-A'₁; right phenyl bears CO₂H and N=N-A'₂.

| Example Nr. | Compound Nr. | A'₁ | A'₂ |
|---|---|---|---|
| 431 | (521) | 5-methyl-3-methyl-2-hydroxy-benzoic acid substituent (CO₂H, OH, CH₃ on phenyl) | 1-phenyl-3-methyl-4-methyl-5-amino-pyrazole |
| 432 | (522) | 4-hydroxy-3-methyl-benzoic acid substituent (HO₂C, OH, CH₃ on phenyl) | 1-phenyl-3-methyl-4-methyl-5-amino-pyrazole |
| 433 | (523) | 4-hydroxy-3-methyl-benzenesulfonic acid substituent (HO₃S, OH, CH₃ on phenyl) | 1-phenyl-3-methyl-4-methyl-5-amino-pyrazole |

APPLICATION EXAMPLES

EXAMPLE 434

Unsized without Filler

A mixture consisting of 50% long fibre spruce sulphite bleached and 50% short fibre beech sulphite bleached fibres is suspended in deionised water, as a 2% suspension, and refined and beaten to 22°SR (Schopper Riegler). After dewatering by means of a centrifuge and testing for dry weight, the equivalent to 10 g of dry fibre are placed in a beaker and made up to a volume of 500 ml with tap water. After stirring for 1 hour, 0.42%, based on the weight of dry fibre, of compound (101) as a 5 g/l aqueous solution are added to the furnish suspension and stirring continued for a further 15 minutes. The suspension is made up to 700 ml with water and from 300 ml of the resulting suspension a hand sheet is produced using a Lhomargy sheet former. After drying on a cylinder at 90° C. for 12 minutes, a greenish-yellow dyeing is obtained showing excellent bleed-fastness to water, soda and acetic acid and good light-fastness. The backwater from the dyeing is almost colourless.

EXAMPLE 435

Neutral Sized with Filler

A mixture consisting of 50% long fibre spruce sulphite bleached and 50% short fibre beech sulphite bleached fibres is suspended in deionised water, as a 2% suspension, and refined and beaten to 35°SR (Schopper Riegler). After dewatering by means of a centrifuge and testing for dry weight, the equivalent to 10 g of dry fibre and 2 g of dry chalk filler are placed in a beaker and made up to a volume of 500 ml with tap water. After stirring for 1 hour, 0.78%, based on the weight of dry fibre, of compound (101) as a 5g/l aqueous solution are added to the furnish suspension and stirring continued for a further 15 minutes. 2% of alkyl ketene dimer size is then added, the suspension stirred for 30 minutes, 0.05% retention aid added and the suspension stirred vigorously for a further 5 minutes. The suspension is made up to 700 ml with water and from 300 ml of the resulting suspension a hand sheet is produced using a Lhomargy sheet former. After drying on a cylinder at 90° C. for 12 minutes, a greenish-yellow dyeing is obtained showing excellent fastness values. The backwater from the dyeing is only weakly coloured.

The invention claimed is:

1. A compound of the formula (13)

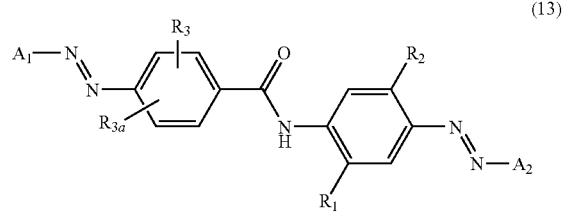

(13)

in which $R_1$ represents hydrogen, $C_1$-$C_4$alkyl, $C_4$-$C_4$alkoxy or $SO_3H$, $R_2$ represents $SO_3H$ or $CO_2H$, $R_3$ represents hydrogen, a $C_1$-$C_4$alkyl group, halogen, hydroxy, $C_1$-$C_4$alkoxy, carboxy, $NH_2$ or $NHC_1$-$C_4$alkyl, $R_{3a}$ represents hydrogen or $NH_2$ and $A_1$ and $A_2$, independently of the other, is selected from the group consisting of an acetoacetylated amine of the formula (2)

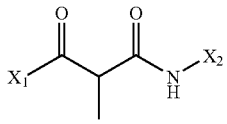
(2)

in which $X_1$ represents $C_1$-$C_4$alkyl, or phenyl which is unsubstituted or monosubstituted by $C_1$-$C_4$alkyl, $C_1$-$C_4$alkoxy or halogen and $X_2$ represents phenyl which is di- or tri-substituted by one or two $SO_3H$, $SO_2NHC_1$-$C_4$alkyl groups which alkyl groups may be substituted, $SO_2C_1$-$C_4$alkyl, $C_1$-$C_4$substituted or unsubstituted alkyl, hydroxy, $C_1$-$C_4$alkoxy, halogen, $CF_3$, $NH_2$, $NHCOC_1$-$C_4$alkyl, $NHCOOC_1$-$C_4$alkyl, $NHCONHC_1$-$C_4$alkyl, $CO_2H$, $CONHC_1$-$C_4$alkyl or $NO_2$;

or $X_2$ is phenyl which is mono-substituted by $SO_3H$, $SO_2NHC_1$-$C_4$ alkyl groups which alkyl groups may be substituted, $SO_2C_1$-$C_4$alkyl, hydroxy, $C_1$-$C_4$alkoxy, $CF_3$, $NH_2$, $NHCOC_1$-$C_4$alkyl, $NHCOOC_1$-$C_4$alkyl, $NHCONHC_1$-$C_4$alkyl, $CO_2H$, $CONHC_1$-$C_4$alkyl or $NO_2$;

or $X_2$ is a 1- or 2-naphthyl residue which is unsubstituted or substituted by one or two $SO_3H$, $SO_2NHC_1$-$C_4$alkyl, carboxy, $CONHC_1$-$C_4$alkyl, carboxy$C_1$-$C_4$alkyl or carboxyaryl groups or a 5- or 6-membered heterocyclic ring containing 1-3 heteroatoms and which may be benzannelated and be further substituted by $C_1$-$C_4$alkyl, $C_1$-$C_4$alkoxy or halogen and which may be attached to the NH-atom in formula (2) either via the hetero- or benzo-nucleus, in the case of benzannelated heterocycles;

a derivative of barbituric acid of the formula (3)

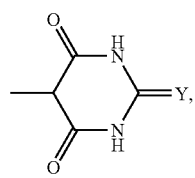
(3)

in which

Y represents O, NCN or $NCONH_2$;

a 2,4,6-triaminopyrimidine derivative;

a pyridone derivative of the formula (4)

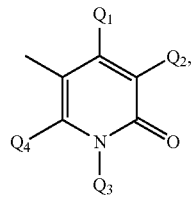
(4)

in which $Q_1$ represents hydrogen, hydroxy, $C_1$-$C_2$alkyl, hydroxyethyl, 2-($C_1$-$C_2$alkoxy)alkyl, $C_1$-$C_2$alkoxy, COOH, $CONH_2$ or $COOC_1$-$C_2$alkyl, $Q_2$ represents hydrogen, CN, $CONH_2$, halogen, $SO_3H$ or $C_1$-$C_2$alkyl which is unsubstituted or substituted by hydroxy, phenyl or $SO_3H$, $Q_3$ represents hydrogen, phenyl, $C_1$-$C_2$alkylphenyl, cyclohexyl or $C_1$-$C_4$alkyl which is unsubstituted or substituted by hydroxy, CN, $C_1$-$C_2$alkoxy or $SO_3H$ and $Q_4$ represents hydrogen or hydroxy;

an aminopyrazole or a pyrazolone derivative of formula (5), (6), (7) or (8)

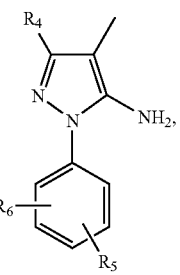
(5)

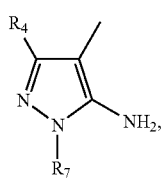
(6)

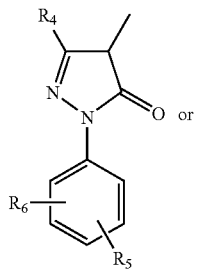
(7)

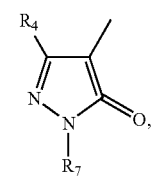
(8)

in which $R_4$ represents hydrogen, substituted or unsubstituted $C_1$-$C_4$alkyl, $C_2$-$C_4$alkenyl, $NHCOC_1$-$C_4$alkyl or $CO_2H$, $R_5$ represents hydrogen, halogen, $C_1$-$C_4$alkyl, $SO_3H$ or $CO_2H$, $R_6$ represents halogen, $C_1$-$C_4$alkyl, $SO_3H$ or $CO_2H$ in formula (5) and represents halogen, $SO_3H$ or $CO_2H$ in formula (7); and $R_7$ represents hydrogen or $C_1$-$C_4$alkyl; and a benzoic acid derivative of formula (9) or (10)

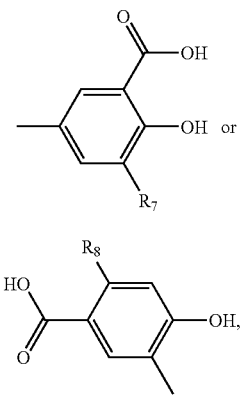

(9)

(10)

in which $R_7$ represents hydrogen or $C_1$-$C_4$alkyl and $R_8$ represents hydrogen or hydroxy, or $A_1$ and $A_2$, each one independently of the other, represent a phenol residue of the formula (11) or (12)

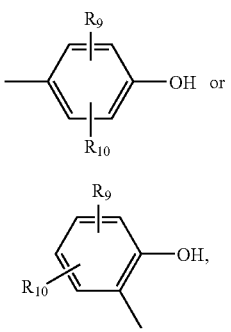

(11)

(12)

in which $R_9$ and $R_{10}$, each one independently of the other, represent hydrogen, $C_1$-$C_4$alkyl, $C_1$-$C_4$alkoxy, hydroxy, halogen, $NH_2$, $NHCOC_1$-$C_4$alkyl, $NO_2$, $SO_3H$, $CO_2C_1$-$C_4$alkyl or $CONHC_1$-$C_4$alkyl groups, with the proviso that in the compounds of formula (13), if $R_1$, $R_2$, $R_3$ and $R_{3a}$ each, independently of the others, are hydrogen or $SO_3H$, then $A_1$ and $A_2$ are not both a 1-phenyl or 1-sulphophenyl-3-methyl-5-aminopyrazole residue, or, if $R_1$, $R_3$ and $R_{3a}$ are hydrogen and $R_2$ is $SO_3H$ and one of $A_1$ and $A_2$ represents a 1-sulphophenyl-3-methyl pyrazol-5-one residue, then the other is not a residue of formula (11) in which both $R_9$ and $R_{10}$ are hydrogen, or if $A_1$ represents a 1-nitrophenyl-, a 1-phenyl- or an unsubstituted 3-methyl pyrazol-5-one residue, $A_2$ is not a residue of formula (9) in which $R_7$ represents hydrogen, or if $R_1$, $R_3$ and $R_{3a}$ represent hydrogen, $R_2$ is $CO_2H$ and $A_1$ represents a residue of formula (9), in which $R_7$ is hydrogen, $A_2$ is not a residue of formula (2) or formula (7).

2. A compound of formula (13) according to claim 1, in which $R_3$ and $R_{3a}$ both represent hydrogen and $A_1$ and $A_2$, each one independently of the other, is selected from the group consisting of an acetoacetylated amine of the formula (2)

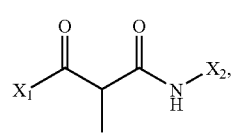

(2)

in which $X_1$ represents $C_1$-$C_4$alkyl, and $X_2$ represents phenyl, which is di- or tri-substituted by $SO_3H$, $C_1$-$C_4$alkyl, hydroxy, $C_1$-$C_4$alkoxy, halogen or $CO_2H$;

or $X_2$ represents phenyl which is mono-substituted by $SO_3H$, hydroxy or $CO_2H$;

barbituric acid or cyanoiminobarbituric acid;

2,4,6-triaminopyrimidine;

citrazinic acid;

a pyridone derivative of the formula (4)

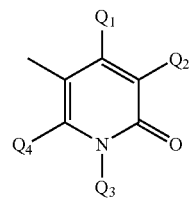

(4)

in which $Q_1$ represents $C_1$-$C_2$alkyl, $Q_2$ represents CN, $CONH_2$ or $CH_2SO_3H$, $Q_3$ represents $C_1$-$C_2$alkyl and $Q_4$ represents hydroxy;

an aminopyrazole or a pyrazolone derivative of formula (5) or (7)

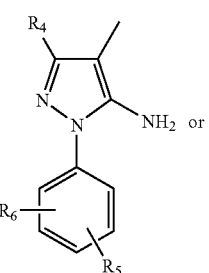

(5)

-continued

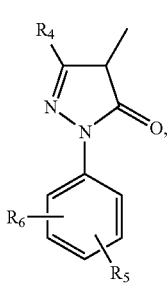

in which
R$_4$ represents C$_1$-C$_4$alkyl or CO$_2$H; and
a benzoic acid derivative of formula (9) or (10)

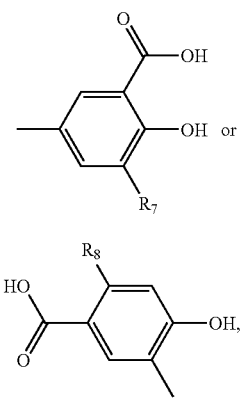 (9)

(10)

in which
R$_7$ represents hydrogen or C$_1$-C$_4$alkyl and
R$_8$ represents hydrogen or hydroxy, or
A$_1$ and A$_2$, each one independently of the other, represent a phenol residue of the formula (11) or (12)

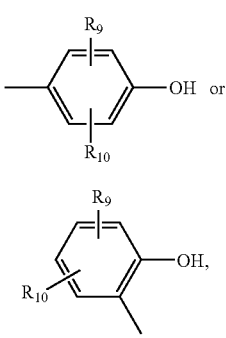

(11)

(12)

in which
R$_9$ represents hydrogen, C$_1$-C$_4$alkyl, C$_1$-C$_4$alkoxy, hydroxy, halogen or SO$_3$H and
R$_{10}$ represents hydrogen.

3. A process for the preparation of a compound of formula (13), according to claim 1, by tetrazotisation of a diaminobenzanilide derivative of the formula

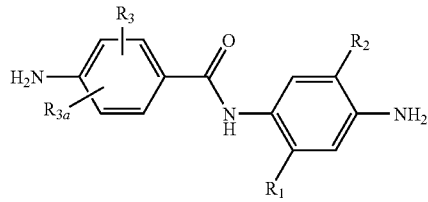

and sequential coupling with a coupling component of the formula A$_1$H or A$_2$H, followed by coupling with a coupling component of the formula A$_2$H or A$_1$H.

4. A process for dyeing natural or synthetic materials, comprising contacting said materials with a tinctorially effective amount of a compound of the formula (13) according to claim 1, and, optionally, further auxiliaries.

5. A solid dye preparation for dyeing paper, comprising a compound of the formula (13) according to claim 1, and, optionally, further auxiliaries.

6. Aqueous solutions for dyeing paper, comprising a compound of the formula (13), according to claim 1, and, optionally, further auxiliaries.

7. Aqueous solutions according to claim 6 containing, as further auxiliaries, solubilizers and/or organic solvents.

8. Paper which is dyed with a compound of the formula (13), according to claim 1.

9. A process for the preparation of a compound of formula (13), according to claim 1, by tetrazotisation of a diaminobenzanilide derivative of the formula

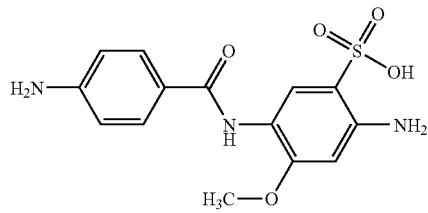

and sequential coupling with a coupling component of the formula A$_1$H or A$_2$H, followed by coupling with a coupling component of the formula A$_2$H or A$_1$H.

* * * * *